US008771677B2

(12) United States Patent
Serikov et al.

(10) Patent No.: US 8,771,677 B2
(45) Date of Patent: Jul. 8, 2014

(54) COLONY-FORMING UNIT CELL OF HUMAN CHORION AND METHOD TO OBTAIN AND USE THEREOF

(76) Inventors: Vladimir B Serikov, Emeryville, CA (US); Frans A Kuypers, El Cerrito, CA (US)

( * ) Notice: Subject to any disclaimer, the term of this patent is extended or adjusted under 35 U.S.C. 154(b) by 440 days.

(21) Appl. No.: 12/591,857

(22) Filed: Dec. 3, 2009

(65) Prior Publication Data

US 2010/0166716 A1 Jul. 1, 2010

Related U.S. Application Data

(60) Provisional application No. 61/203,648, filed on Dec. 29, 2008.

(51) Int. Cl.
*A01N 63/00* (2006.01)
(52) U.S. Cl.
USPC .......................... 424/93.7; 435/366; 435/325
(58) Field of Classification Search
USPC ....................................................... 424/93.7
See application file for complete search history.

(56) References Cited

U.S. PATENT DOCUMENTS

| | | | |
|---|---|---|---|
| 3,862,002 A | 1/1975 | Sanders |
| 5,486,359 A | 1/1996 | Caplan |
| 5,583,131 A | 12/1996 | Bridger |
| 5,942,225 A | 8/1999 | Bruder |
| 5,962,325 A | 10/1999 | Naughton |
| 6,326,019 B1 | 12/2001 | Tseng |
| 6,338,942 B2 | 1/2002 | Kraus |
| 7,029,666 B2 | 4/2006 | Bruder |
| 7,045,148 B2 | 5/2006 | Hariri |
| 7,118,746 B1 | 10/2006 | Naughton |
| 7,255,879 B2 | 8/2007 | Hariri |
| 7,311,905 B2 | 12/2007 | Hariri |
| 7,399,632 B2 | 7/2008 | Simmons |
| 7,413,734 B2 | 8/2008 | Mistry |
| 7,468,276 B2 | 12/2008 | Hariri |
| 7,498,171 B2 | 3/2009 | Hariri |
| 7,510,873 B2 | 3/2009 | Mistry |
| 7,524,489 B2 | 4/2009 | Messina |
| 7,534,606 B2 | 5/2009 | Chen |
| 7,547,546 B2 | 6/2009 | Davies |
| 7,560,276 B2 | 7/2009 | Harmon |
| 2003/0235563 A1 | 12/2003 | Strom |
| 2004/0048372 A1 | 3/2004 | Hariri |
| 2004/0107453 A1 | 6/2004 | Furtch |
| 2004/0136967 A1 | 7/2004 | Weiss |
| 2004/0161419 A1 | 8/2004 | Strom |
| 2005/0054093 A1 | 3/2005 | Haas |
| 2005/0124003 A1 | 6/2005 | Atala |
| 2005/0176139 A1 | 8/2005 | Chen |
| 2006/0154366 A1 | 7/2006 | Brown |
| 2006/0154367 A1 | 7/2006 | Kihm |
| 2006/0166361 A1 | 7/2006 | Seyda |
| 2006/0171930 A1 | 8/2006 | Sayda |
| 2006/0188983 A1 | 8/2006 | Harris |
| 2006/0222634 A1 | 10/2006 | Clarke |
| 2006/0233765 A1 | 10/2006 | Messina |
| 2006/0233766 A1 | 10/2006 | Messina |
| 2006/0234376 A1 | 10/2006 | Mistry |
| 2006/0281178 A1 | 12/2006 | Sakuragawa |
| 2007/0092497 A1 | 4/2007 | Hariri |
| 2007/0134210 A1 | 6/2007 | Heidaran |
| 2007/0190034 A1 | 8/2007 | Paludan |
| 2007/0190042 A1 | 8/2007 | Edinger |
| 2007/0275362 A1 | 11/2007 | Edinger |
| 2008/0032401 A1 | 2/2008 | Edinger |
| 2008/0131410 A1 | 6/2008 | Hariri |

FOREIGN PATENT DOCUMENTS

| | | |
|---|---|---|
| WO | WO/2005/001079 | 1/2005 |
| WO | WO/2005/001080 | 1/2005 |
| WO | WO/2005/003334 | 1/2005 |
| WO | WO/2006/071777 | 6/2006 |
| WO | WO/2006/071778 | 6/2006 |
| WO | WO/2006/071794 | 6/2006 |
| WO | WO/2006/071802 | 6/2006 |
| WO | WO/2006/071773 | 7/2006 |
| WO | WO/2008/019148 | 2/2008 |
| WO | WO/2008/100498 | 8/2008 |
| WO | WO/2008/156659 | 12/2008 |

OTHER PUBLICATIONS

Alviano F, Fossati V, Marchionni C, Arpinati M, Bonsi L, Franchina M, Lanzoni G, Cantoni S, Cavallini C, Bianchi F, Tazzari PL, Pasquinelli G, Foroni L, Ventura C, Grossi A, GP Bagnara. Term amniotic membrane is a high throughput source for multipotent mesenchymal stem cells with the ability to differentiate into endothelial cells in vitro. BMC Dev Biology, 2007; 7:11-18.

Bailo M, Soncini M, Vertua E, Signoroni PB, Sanzone S, Lombardi G, Arienti D, Calamani F, Zatti D, Paul P, Albertini P, Zorzi F, Cavagnini A, Candotti F, Wengler GS, O Parolini. Engraftment potential of human amnion and chorion cells derived from term placenta. Transplantation, 2004; 78:1439-1448.

Chien C-C, Yen BL, Lee F-K, Lai T-H, Chen Y-C, Chan S-H, HI Huang. In vitro differentiation of human placenta-derived multipotent cells into hepatocyte-like cells. Stem Cells, 2006; 24:1759-1768.

De Coppi P, Bartsch G, Siddiqui MM, Tao XU, Santos CC, Perin L, Mostoslawsky G, Serre AC, Snyder EY, Yoo JJ, Furth ME, Soker S, A. Atala. Isolation of amniotic stem cell lines with potential for therapy. Nature Biotechnology, 2007; 25:100-106.

Dominici M, Leblank K, Mueller I, Slaper-Cortenbach I, Marini FC, Krause DS, Deans RJ, Keating A, Prockop DJ, Horwitz EM. Minimal criteria for defining miltipotent mesenchymal stem cells. The international Society for Cellular Therapy position statement. Cytotherapy, 2006; 8:315-317.

Fukuchi Y, Nakagima H, Sugiyama D, Hirose I, Kitamura T, K. Tsuji. Human Placenta-Derived cells have mesenchymal stem/progenitor cell potential. Stem Cells, 204; 22: 649-658.

(Continued)

Primary Examiner — Jon P Weber
Assistant Examiner — Tiffany Gough
(74) Attorney, Agent, or Firm — Goodwin Procter LLP

(57) ABSTRACT

The present invention features colony-forming unit cells derived from the chorion of human placenta and describes compositions and methods for the uses of chorionic cells and their products for therapeutic purposes based upon production and release of multiple growth factors and cytokines by these cells stimulating tissue regeneration independent of engraftment, as well as differentiation into a specific cell type.

10 Claims, 8 Drawing Sheets

(56) References Cited

OTHER PUBLICATIONS

Ilancheran, S, Michalska A, Peh G, Wallace EM, Pera M, U Manuelpillai. Stem Cells Derived from Human Fetal Membranes Display Multilineage Differentiation Potential. Biology of Reproduction, 2007; 77:577-588.

Int' Anker PS, Scherjon SA, Van Der Keur CK, De Groot-Swings GMJS, Claas FHJ, Fibbe WE, HHH Kanhai. Isolation of Mesenchymal stem cells of fetal or maternal origin from human placenta. Stem Cells, 2004; 22:1338-1345.

Linju Yen B, Hsing-I Huang, Chih-Cheng Chien, Hsiang-Yiang Jui, Bor-Sheng Ko, Ming Yao, Chia-Tung Shun, Men-Luh Yen, Meng-Chou Lee, Yao-Chang Chen. Isolation of Multipotent Cells from Human Term Placenta. Stem Cells, 2004; 23:3-9.

Matikainen T., Laine, J. Placenta—an alternative source of stem cells. Toxicol. Appl. Pharmacol, 2005, 207 (2 Suppl), 544-549.

Ming-Song, Shiaw-Min Hwangc, Kuang-Den Chend, Yun-Shien Leee, Li-Wen Hsuc, Yu-Jen Changc, Chao-Nin Wangg, Hsiu-Huei Pengg, Yao-Lung Changg, An-Shien Chaog, Shuenn-Dyh Chang, Kuan-Der Leeh, Tzu-Hao Wangf, Hsin-Shih Wang, Yung-Kuei Soong. Functional Network Analysis of the Transcriptomes of Mesenchymal Stem Cells Derived from Amniotic Fluid, Amniotic Membrane, Cord Blood, and Bone Marrow. Stem Cells, 2007; 25:2511-2523.

Zhao P, Ise H, Hongo M, Ota M, Konishi I, Nikaido. Human amniotic mesenchymal cells have some characteristics of cardiomyocytes. Transplantation, 2005; 79: 528-535.

Miki T, Lehmann T, Hongbo Cai, Stolz DB, SC Strom. Stem Cell Characteristics of Amniotic Epithelial Cells. Stem Cells, 2005; 23: 1549-1559.

Miki T, Mitamura K, Ross MA, Stolz DB, SC Strom. Identification of stem cell marker-positive cells by immunofluorescence in term human amnion. J Reprod Immunol, 2007; 75: 91-96.

Parolini O, Alviano F, Bagnara GP, Bilic G, Buhring HJ, Evangelista M, Hennerbichler S, Bing Liu, Magatti M, Ning Mao, Toshio Miki, Marongiu F, Hideaki Nakajima, Toshio Nikaido, Portmann-Lanz CB, Sankar V, Soncini M, Stadler G, Surbek D, Tsuneo A. Takahashi, Redl H, Norio Sakuragawa, Wolbank S, Zeisberger S, Zisch A, SC Strom. Isolation and Characterization of Cells from Human Term Placenta: Outcome of the First International Workshop on Placenta Derived Stem Cells. Stem Cells, Nov. 2007.

Portmann-Lanz CB, Schoeberlein A, Huber A, Sager R, Malek A, Holzgreve W, DV Surbek. Placental mesenchymal stem cells as potential autologous graft for pre- and perinatal neuroregeneration. Am J Obstet Gynecol, 2005; 194: 664-73.

Sakuragawa N, Enosawa S, Ishii T. Thangavel R, Tashiro T, Okuyama T, S Suzuki. Human amniotic epithelial cells are promising transgene carriers for allogeneic cell transplantation into liver.J Hum Genet, 2000; 45: 171-6.

Sakuragawa N, Kakinuma K, Kikuchi A, Okano H, Uchida S, Kamo I, Kobayashi M, Y Yokoyama. Human amnion mesenchyme cells express phenotypes of neuroglial progenitor cells. J Neurosci Res, 2004; 78: 208-14.

Soupene E, Serikov V, Kuypers FA. Characterization of an acetyl-coenzyme A binding protein predominantly expressed in human primitive progenitor cells. J. Lipid Res. 2004; 49:1103-12.

Tamagawa T, Ischiwata I, S.Saito. Establishment and characterization of a pluripotent stem cell line derived from human amniotic membranes and initiation of germ layers in vitro. Hum Cell, 2004; 17: 125-130.

Uchida S, Inanaga Y, Kobayashi M, Hurukawa S, Araie M, Sakuragawa N. Neurotrophic function of conditioned medium from human amniotic epithelial cells. J Neuroscience Research, 2000; 62:585-590.

Wolbank S, Peterbauer A, Fahrner M, Hennerbichler S, Van Griensven M, Stadler G, Redl H, Gabriel C. Dose-dependent immunomodulatory effect of human stem cells from amniotic membrane: a comparison with human mesenchymal stem cells from adipose tissue. Tissue Eng, 2007; 13: 1173-83.

Zhang X, Mitsuru A, Igura K, Takahashi K, Ichinose S, Yamaguchi S, Takahashi T. Mesenchymal progenitor cells derived from chorionic villi of human placenta for cartilage tissue engineering. Biochem Biophys Res Commun, 2006: 340: 944-952.

 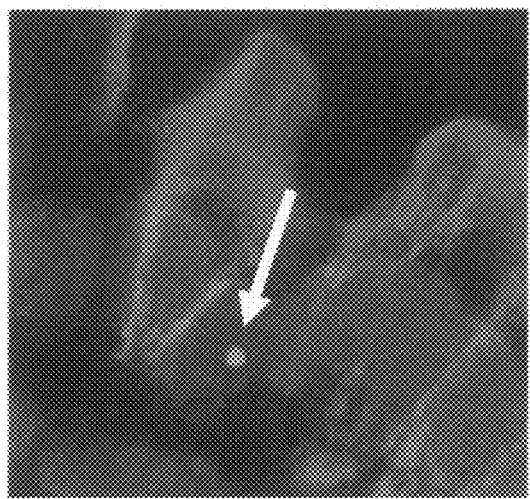
Fig. 7A
Fig. 7B

COLONY-FORMING UNIT CELL OF HUMAN CHORION AND METHOD TO OBTAIN AND USE THEREOF

CROSS-REFERENCE

This application claims the benefits of U.S. Provisional Patent Application No. 61/203,648 filed on Dec. 29, 2008 which application is incorporated herein by reference.

BACKGROUND

Derivation, characterization and therapeutic use of stem cells is among the most rapidly-developing fields of modern biology and medicine. Ability of stem cells differentiate into many lineages, as well as significantly influence processes of tissue regeneration paves the way for wide use of stem cell-based therapies in many medical applications. Multiple types of stem cells, embryonic and adult, are currently investigated. Though embryonic and induced pluripotent stem cells may be differentiated into any other cell types, their ability to form teratomas currently precludes their use in medical practice. Adult stem cells are currently used in humans, though only hematopoietic stem cells have been proven to provide therapeutic effect. One of the main problems is the difficulty in obtaining sufficient amount of stem cells, maintaining their "stemness" potential while in culture. Therefore, supply of stem cells is very limited, and novel sources are in high demand.

Human embryonic stem cells are derived from the pre-implantation or peri-implantation embryo and are characterized by the following major features: prolonged undifferentiated proliferation and stable developmental potential to form all the three of germ layers even after prolonged culture. Prolonged undifferentiated proliferation of human ECS is achieved by growing these cells on mouse embryonic fibroblast feeder layers in special ECS medium. Other specific features of human ESC, including: 1) high levels of telomerase activity; 2) formation of embryonic bodies; 3) expression of specific cellular markers Oct-4, Nanog, Sox-2 and surface markers CD117, SSEA-3, SSEA-4, TRA-1-60, TRA-1-81 and alkaline phosphatase activity; and 4) formation of teratomas in immuno-compromised animals, are used to confirm derivation of pluripotent stem cell lines, similar to ECS.

Mesenchymal stem cells (MSC) are derived from adult body. Currently the most widely used and well characterized source of MSC is bone marrow. The basic features of adult mesenchymal stem cells (MSC) are: 1) proliferation potential; 2) the ability to differentiate; 3) plasticity; and 4) the ability to adhere to plastic, promoting the basic procedure for the MSC isolation, storage and usage. The MSC are characterized by expression of many common molecules required for adherence to solid surface and cell to cell interactions (Dominici et al., 2005). MSC possess a rich differential potential allowing them to differentiate into almost all possible mesenchymal lineages except hematopoietic cells. Several technical difficulties exist in practical approaches for obtaining stem cell populations from different organs of adult tissue due to very low occurrence of stem cells (fractions of a percent) and clear ethical problems associated with embryos or fetuses. Harvesting stem cells from adult sources such as bone marrow is labor-intensive and expensive. Harvesting stem cells from an adult donor, which is a current practice for obtaining hematopoietic cells and stromal cells of bone marrow possesses certain threats to donor, is expensive, labor-intensive and effective transplantation requires immunological match between donor and recipient.

Placenta, as a discarded material after birth, represents a unique opportunity for harvest of autologous or allogeneic populations of stem cells. Stem cells derived from feto-placental complex have been previously described. Stem cells of amniotic fluid have been described in many studies (Alviano et al, 2007; in't Anker et al, 2004). Stem cells isolated from human-term amniotic fluid may be cultured over 50 population doublings (in'tAnker et al, 2004). Phenotype of these cells was close to phenotype of MSC from bone marrow by expression of CD90, CD105, CD166, CD49, SH3, SH4 and negative for CD31, CD34, CD45, HLA-DR. However, at third trimester of pregnancy the viability of these cells decreases substantially and only in 20% it was possible to obtain viable stem cells from amniotic fluid. Embryonic-like stem cells in amniotic fluid are identified by expression of Oct-4, stem cell factor (SCF), high telomerase activity. Report by DeCoppi et al (2007) describes stem cell lines isolated from amniotic fluid following enrichment of c-kit positive cells. These cells expand without feeders up to 250 population doublings, are not tumorigenic, and can be differentiated into cell types representing cells of all the germ layers.

Yet another source of MSC is human placenta itself (Fukuchi Y et al, 2004; Matikainen T, Laine J. 2005). Previous studies (Linjuy Yen et al, 2005) demonstrated that multipotent, multilineage cells were present in the human term placenta. Although the initial cell culture consisted of both fibroblastoid and non-fibroblastoid cell types, only the fibroblastoid population remained after enzymatic digestion and passaging. MSC markers such as CD105/endoglin/SH-2 and SH-3, SH-4, integrins and matrix receptors displayed by placental stem cells, suggesting that these cells resemble MSC from the bone marrow. This is further supported by their fibroblastoid morphology, plastic-adherence nature, and mesodermal differentiation capabilities. In addition to MSC markers, cell surface markers SSEA-4, TRA-1-60, and TRA-1-81 were present on placenta-derived cells, which were previously found only in embryonic stem and germ cells.

First International Workshop on placenta-derived stem cells (Parolini et al, 2007) suggested the following nomenclature for cells derived from fetal placenta: Amniotic Epithelial Cells (hAEC), Amniotic mesenchymal Stromal cells (hAMSC), Chorionic Mesenchymal Stromal Cells (hC-MSC), and Chorionic Trophoblastic Cells (hCTC) and suggested that cells isolated from fetal membranes should be termed mesenchymal stromal cells. Minimal criteria for defining these cells were adherence to plastic, formation of colonies, specific pattern of surface antigen expression and differentiation potential. hAEC were extensively studied by the group of S. Strom, (Miki et al, 2005, 2007). Cells obtained from amniotic membrane are phenotypically heterogeneous, could proliferate up to 5-10 passages and express very low levels of HLA-A,B,C. These cells express markers of pluripotent cells such as SSEA-3 and -4, TRA-1-60 and TRA-1-81, Oct-4, SOX-2 and Nanog. Such hAMC are capable to differentiate into the cells of all three germ layers (Tamagawa et al, 2004, Ilancheran et al, 2007). According to reports (Chien et al, 2006; Miki et al 2005; Sakuragawa et al, 2000), hAMC can be differentiated into hepatic-like cells. Differentiation of hAEC into neuronal-like (Sukuragawa, 2004) was reported. Functional genomic studies by Ming-Song Tsaia et al (2007) revealed that core gene expression profiles were preserved in those four kinds of MSC from amniotic fluid, amniotic membrane, cord blood and bone marrow. The core signature transcriptomes of all MSCs, in comparison with those of fetal organs, included genes involved in the regulation of extracellular matrix and adhesion, transforming growth factor-β receptor signaling, and the Wnt signaling pathways.

Mesenchymal stem cells of placenta: hAMSC and hCMSC are likely to originate from extraembryonic mesoderm. hAMSC were characterized in several publications (Surakagawa et al, 2004; int'Anker et al, 2004; Portmann-Lanz et al, 2006; Wolbank et al, 2007), though descriptions of hCMSC are very limited (Zhang et al, 2006). Profile of surface marker expression on hAMSC and hCMSc is close to bone marrow-derived MSC as both are positive for CD90 and CD105, but do not express markers of hematopoietic of leukocyte markers (Portmann-Lanz et al, 2006; Alviano et al, 2007; Zhao et al, 2005). Differentiation of hAMSC and hCMSC was demonstrated towards mesodermal lineages, while hAMSC could be induced to differentiate into neural (ectoderm) and pancreatic cells (endoderm) (Parolini et al, 2007). However, as hAMSC and hCMSC described in the above cited publications were derived by plastic-adherence techniques, they represent mixed populations and clones of multiple different stem and progenitor cells. Since these cells are not clonally-derived, their pluri- or multipotency remains unproven. Qualitative evidence of engraftment of chorionic and amniotic cells in newborn rat and swine was detected only by RT-PCR, without morphological evidence of engraftment and/or differentiation in tissues (Bailo et al, 2004).

Thus, though amniotic epithelial and amniotic mesenchymal stem cells have been studied in several reports over the past decade, information on chorionic mesenchymal and/or other stem cells has been not presented yet. Clonal-derived stem cell lines have not been described. Cell lines so far isolated from mesenchyme of placenta, have been characterized by limited capability of proliferation (only 5-10 passages). Mesenchymal cells from chorion have not been characterized by their ability to differentiate into cells of all three germ layers, nor have they been reported for their ability to engraft tissues of animals, differentiate in tissues, or form tumors. Further, placental tissue has not been yet reported for the presence of primitive pluripotent cells, different from mesenchymal stomal plastic-adherent cells.

The subject matter of this invention are novel stem cell populations originating from chorion of human placenta, termed chorionic colony-forming unit cells (CCFUC) which are uniquely characterized by expression of novel acetyl-coenzyme A binding protein (ACBD6) described in placental chorionic stromal stem cells by us (Soupene et al, 2008) and references therein.

Human mesenchymal stem cells of different origin have been a subject of multiple patents. Most of patents describe cells, capable of differentiation in connective tissue type, obtained from bone marrow, adhere to plastic, positive for surface markers SH2, SH3, SH4 (Caplan, U.S. Pat. No. 5,486,359 "Human mesenchymal stem cells"). Methods of directed differentiation of such stem cells ex vivo are further described (Bruder et al., U.S. Pat. No. 5,942,225 "Lineage-directed induction of human mesenchymal stem cell differentiation"). Methods and systems are described for selective expansion of target cell populations, and methods of treating patients with cell populations and products (Krauss et al., U.S. Pat. No. 6,338,942 "Selective expansion of target cell populations"), as well as methods of using non-autologous mesenchymal stem cells comprising treating a recipient (Bruder et al., U.S. Pat. No. 7,029,666 "Uses for non-autologous mesenchymal stem cells"). Simmons et al., describes mesenchymal precursor cells based upon expression of STRO-1 (U.S. Pat. No. 7,399,632 "Mesenchymal precursor cell").

Placenta and its parts as a source of stem cells and physiologically active substances has been a subject of patents. Sanders (U.S. Pat. No. 3,862,002 "production of physiologically active placental substances") teaches a system, in which viable placental tissue is placed in circulating culture medium and processed culture medium is then removed from tissue and desired substances are withdrawn. Limitations of this technique are based upon the fact that such method does not teach isolation of stem cell population. Also, such technique provides very low yield of cells as cells remain attached to tissue matrix.

Tseng (U.S. Pat. No. 6,326,019 "Grafts made from amniotic membrane") teaches a method for making surgical grafts from amniotic membrane. As amnion represents only a very small fraction of placental tissue—less than 5%, yield of viable colony-forming unit cells from this specific source is very low. Low yield of primary cells requires multiple steps of cell passaging in order to obtain amount of cells required for therapeutic use in humans (about 100 million cells). Multiple passages in turn significantly increase the risk of chromosomal aberrations in cultured cells, making it highly risky for therapeutic use. Amniotic epithelial cells form teratomas and, therefore, can not be readily used in humans.

Cells isolated from umbilical cord—anatomical structure which connects a baby with placenta—have been described in several patents. Messina et al., (U.S. Pat. No. 7,524,489 "Regeneration and repair of neuronal tissue using postpartum-derived cells"), teaches method of treatment patients with cells derived from umbilical cord which do not express CD117 while expressing oxidized LDL receptor interleukin 8 or reticulon 1. Mistry et al., (U.S. Pat. No. 7,510,873 "Postpartum cells isolated from umbilical cord tissue, and methods of making and using the same") teaches method of isolation of a cell from umbilical cord by enzymatic digestion that does not express CD117, CD31, CD34, CD141 or CD45 and express CD10, CD13, CD44, CD73, CD90, PDGFr-alpha or HLA-A, and further teaches use of these cells for treatment of retinitis (Mistry et al., U.S. Pat. No. 7,413,734 "Treatment of retinitis pigmentosa with human umbilical cord cells"). Harmon et al. (U.S. Pat. No. 7,560,276 "Soft tissue repair and regeneration, using postpartum-derived cells") teaches use of these cells from umbilical cord and their products for soft tissue repair. Davies et al., U.S. Pat. No. 7,547,546 "Progenitor cells from Wharton's jelly of human umbilical cord" teaches obtaining cells from umbilical cord and their use in tissue repair. Use of proteolytic enzymes required for all the above described methods, first, dramatically reduces cell viability and yield of colony-forming unit cells, and, second, eliminates expression of many stem cell markers on cell surface, thus not allowing using sorting techniques for isolation of stem cells. The above described methods to obtain cells from umbilical cord feature same problems as obtaining stem cells from other low volume sources—yield of viable colony-forming unit cells from this source is very low. Low yield of primary cells requires multiple steps of cell passaging in order to obtain amount of cells required for therapeutic use in humans, while passaging increases the risk of chromosomal aberrations and tumor formation. Such risk of tumor formation from human fetal cells is more than real, and clinical cases of brain tumor development in patient from transplanted cells following administration of fetal cells were reported. It is, therefore, a subject matter of this invention to disclose novel techniques, methods and stem cell populations which could be obtained from the largest (95% of tissue mass of placenta) portion of placenta which allows to obtain very large yield of primary cells (several billion primary stem cells) without the use of proteolytic enzymes. Chen et al., (U.S. Pat. No. 7,534,606 "Placental stem cells and methods thereof") claims a method of neurogenic differentiation of human placental stem cells, comprising culturing of placental stem cells in medium comprising an effective amount of 1-methyl-3-isobytylxantine.

Hariri (U.S. Pat. No. 7,045,148) reports that the first collection of blood from the perfused placenta, referred to as cord blood, contains populations of hematopoietic progenitor cells which are CD34 positive and CD38 positive or CD34 positive and CD38 negative or CD34 negative and CD38 positive. Subsequent perfusions of the placenta were reported to yield embryonic-like stem cells that are SSEA-3 negative, SSEA-4 negative, Oct-4 positive, ABC-p positive, CD10 positive, CD38 negative, CD29 positive, CD34 negative, CD44 positive, CD45 negative, CD54 positive, CD90 positive, SH2 positive, SH3 positive and SH4 positive. Hariri (U.S. Pat. No. 7,311,905 "Embryonic-like stem cells derived from post-partum mammalian placenta, and uses and methods of treatment using said cells") describes a composition of human stem or progenitor cells that are positive for SH2, SH3, SH4 and Oct-4, while negative for CD34, CD45, SSEA3 and SSEA4, and obtained from placenta that has been drained from cord blood. Cells could express at least one of the following markers: CD10, CD29, CD44, CD54, CD90. Hariri (U.S. Pat. No. 7,468,276 "Placental stem cells") describes the same placental stem cell population, adherent to plastic. Hariri (U.S. Pat. No. 7,255,879 "Post partum mammalian placenta, its use and placental stem cell populations") teaches method to obtain the above described placental stem cell population by perfusing placenta via circulation with a perfusion solution containing an anticoagulant, growth factor or cytokine selected from a group consisting of a colony stimulating factor, interferon, erythropoietin, stem cell factor, thrombopoietin, an interleukin, granulocyte colony-stimulating factor, and any combination thereof, and collection of cells from perfusate. Methods of directed differentiation of these cells are described by Hariri (U.S. Pat. No. 7,498,171 "Modulation of stem and progenitor cell differentiation, assays and uses thereof"). The main disadvantage of methods described by Hariri in the above cited patents is in the fact that long-term perfusion of placenta is required to obtained claimed cells. It is know to those skilled in arts that in most cases of placentas obtained by Caesarian section and in all cases of placentas collected following natural birth, placentas are ruptured. This precludes the possibility of the long-term perfusion, as perfusate is rapidly lost via ruptures of chorion; therefore, long-term perfusion becomes unworkable. In most cases, arteries of umbilical cord rapidly completely constrict, and as thrombosis develops in placental vessels perfusion of placenta by techniques claimed by Haririr's patents (U.S. Pat. No. 7,045,148; U.S. Pat. No. 7,255,879; U.S. Pat. No. 7,311,905; U.S. Pat. No. 7,468,276) becomes practically impossible. Most importantly, perfusion of placenta via natural circulation does not allow collecting populations of stem cells which are located in stroma, interstitial tissue or non-perfused regions of placental circulation. Therefore, placental perfusion and cells claimed by Hariri's patents (U.S. Pat. No. 7,045,148; U.S. Pat. No. 7,311,905; U.S. Pat. No. 7,468,276; U.S. Pat. No. 7,498,171) allow obtaining very restricted and limited cell populations present in placenta, which belong to pool located inside the circulatory space. It is, therefore, a subject matter of this invention to disclose novel techniques, methods and stem cell populations which could be obtained without placental perfusion and collection of perfusate, as well as without the use of proteolytic enzymes. Placental stem cell populations and compositions of placental stem cells described by Hariri (U.S. Pat. No. 7,045,148; U.S. Pat. No. 7,311,905; U.S. Pat. No. 7,468,276) are characterized only by expression of several classical surface antigens (CD34, CD45, SSEA, SH-2, SH3, SH4, CD38, CD10, CD29, CD44, CD54, CD90). Moreover, Hariri wrongfully claims that cells described in these patents bear Oct-4 as surface marker (for example U.S. Pat. No. 7,311,905, claim 15), while Oct-4 is cytosolic/nuclear protein which is not expressed on surface of any cell, including embryonic stem cells. Placental cells claimed by Hariri (U.S. Pat. No. 7,045,148; U.S. Pat. No. 7,311,905; U.S. Pat. No. 7,468,276) are not characterized by their ability to form colonies, produce clones, differentiate into lineages of any of germ layers, form or not form teratomas, engraft immuno-compromised animals of humans, therefore differentiation potential and "sternness" of claimed cells is unknown. It is, therefore, a subject matter of this invention to disclose novel techniques, methods and stem cell populations from placenta which demonstrate specific phenotype and ability to form clones, differentiate into lineages of all 3 germ layers and engraft immunocompromized animals without formation of teratomas.

Naugtington et al. (U.S. Pat. No. 5,962,325) claims a method of making a composition comprising culturing fibroblast cells in 3-dimensional conditions. Naugtington et al. (U.S. Pat. No. 7,118,746 "Conditioned cell culture medium compositions and methods of use") claims methods to obtain and use conditioned medium obtained from culture of human mesenchymal cells. The drawbacks of claimed methods is its limitations to secreted factors produced by mesenchymal cells, while stem cells produce different compositions of secreted factors which are more potent in tissue regeneration. Uchida (Uchida et al., 2000) described neurotrophic function of conditioned medium from human amniotic cells.

SUMMARY OF THE INVENTION

The subject matter of this invention is novel population of chorionic colony-forming unit cells. This invention further describes unique phenotypic characteristics of these novel cell populations, placing them among adult stromal cells with some phenotypic features of embryonic cells. Results of functional differentiation assays are provided to demonstrate ability of these cells to differentiate into 3 germ layers under specific conditions without formation of teratomas in immuno-compromised mouse. Finally, unique ability of this novel stem cell population to secrete abundant amounts of growth factors provides basis for their high potency as therapeutic tools which is supported by examples provided.

The present invention describes novel populations of colony-forming unit cells derived from chorion of human term placentas. Particularly, preferred colony-forming cell units derived from chorion possess the characteristics:
I) expression of protein ACBD6,
II) low telomerase activity and ability to be propagated over at least 50 doublings in vitro culture without substantial alteration of karyotype,
III) expression of a combination of at least one of the markers from each of:
  i) CD-90, SSEA-3, TRA-1-60;
  ii) one or more cytosolic polypeptides selected from Nanog, neurofilament family, Nestin, or one or more secreted polypeptides selected from family of fibroblast growth factors, hepatocyte growth factors, keratinocyte growth factors, angiopoietins;
  iii) nuclear peptide Oct-4.
IV) lack the ability of spontaneous differentiation into lineages of 3 germ layers under standard culture conditions, unless specifically stimulated, or lack of ability for formation of teratomas in humans or immuno-compromised animals, V) ability to differentiate under appropriate stimulatory conditions into lineages of all 3 germ layers.

The current invention describes methods for directing the differentiation pathway of these cells towards multiple lineages.

In one preferred embodiment, colony-forming unit cells of human placenta are obtained from placenta by enzymatic or non-enzymatic tissue processing and selected from population of colony-forming units not adherent to plastic.

In another preferred embodiment, placental tissue is mechanically processed without enzymatic digestion followed by filtration through a set of various filters with decreasing pore size, so that final composition contains a mixture of live cells and colony-forming unit cells, which are further selected by sorting and enrichment based upon expression of one or combination of surface markers ACBD6, SSEA-3, TRA-1-60.

In another preferred embodiment CCFUC could be used to treat ischemic disorders of myocardium.

In another preferred embodiment CCFUC could be used to treat injuries of spinal cord or peripheral nerves.

In another preferred embodiment CCFUC could be used to treat muscular dystrophy disorders.

DEFINITIONS

As used herein, the term "colony-forming unit cells" or "stem cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type.

The following terms are used here to refer different types of stem cells: 1. Bone marrow derived mesenchymal stem cell (BMMSC) are multipotent stromal stem cells derived from human bone marrow. 2. Amniotic mesenchymal stem cells (AMSC)—stromal stem cells derived from amniotic mesenchyme. 3. Chorionic colony-forming unit cells (CCFUC)—chorionic stem cells of current invention, derived from chorion of human placenta. 4. Embryonic stem cells (ESC) are stem cells derived from embryo. 5. Perfusion—derived placental stem cells (PDPSC) obtained from placenta perfusate as described by Hariri (U.S. Pat. No. 7,045,148; U.S. Pat. No. 7,311,905; U.S. Pat. No. 7,468,276; U.S. Pat. No. 7,498,171)

Term "infusion" refers to a method of delivery of fluids, compositions, drugs, solutions to tissue and its cellular and extracellular components, not necessarily utilizing vascular bed. Term "perfusion" refers the process of nutritive delivery of blood or its substitute—"perfusate" to the capillary bed of tissue. Term "effusate" refers to cell suspension obtained placental chorion following infusion or perfusion.

This invention is not limited to particular embodiments described, as such may vary.

BRIEF DESCRIPTION OF THE DRAWINGS

FIG. 7. Examples of mouse-human chimerism in multiple organs of mice 6 months after transplantation of chorionic colony-forming unit cells into sublethally irradiated NOD/SCID mice. A: RT-PCR results for human beta-globin gene in chimeric mouse. Lanes: 1—Positive control; 2—Negative control; 3—Intestine; 4—Skeletal muscle; 5—Spleen; 6—Brain; 7—Liver; 8—Lung. Expected PCR product is at 300 BP. B: Human chorionic colony-forming unit cells transform into specific cells of endodermal lineages. Staining for human Y-chromosome with Cy-3 (red)-labeled probe. Intestine, co-staining for cytokeratin 20 (intestinal epithelial cells)—green, indicating endodermal differentiation of chorionic colony-forming unit cells. Magnification ×90, bar is 10 μm.

DETAILED DESCRIPTION OF THE INVENTION

1. General Description.

Particularly preferred colony-forming unit cells derived from chorion are characterized by the following features:

I) expression of protein ACBD6,

II) low telomerase activity and ability to be propagated over at least 50 doublings in vitro culture without substantial alteration of karyotype, III) expression of a combination of at least one of the markers from each of:
   i) CD-90, SSEA-3, TRA-1-60;
   ii) one or more cytosolic polypeptides selected from Nanog, neurofilament family, Nestin, or one or more secreted polypeptides selected from family of fibroblast growth factors, hepatocyte growth factors, keratinocyte growth factors, angiopoietins;
   iii) nuclear peptide Oct-4.
IV) lack the ability of spontaneous differentiation into lineages of 3 germ layers under standard culture conditions, unless specifically stimulated, or lack of ability for formation of teratomas in humans or immuno-compromised animals,
V) ability to differentiate under appropriate conditions into lineages of all 3 germ layers.

2. Colony-Forming Unit Cells: Derivation, Characterization and Propagation

The present invention provides methods for obtaining stem cell or colony-forming unit cells from a mammalian placenta. The methods generally involve: a) obtaining placenta; b) mechanical processing of chorion; c) obtaining cultures of non-adherent cells.

A placenta is obtained following birth, e.g., from one minute to about one hour following birth. For example, a mammalian placenta is obtained from about one minute to about 5 minutes, from about 5 minutes to about 10 minutes, from about 10 minutes to about 20 minutes, from about 20 minutes to about 30 minutes, from about 30 minutes to about 45 minutes, or from about 45 minutes to about 60 minutes following birth.

The amniotic layer is removed to isolate amniotic epithelial and amniotic mesenchymal cells, and the remaining chorions are mechanically disrupted to obtain cell suspensions. Additional non-enzymatic processing may improve yield of cell from placental tissue. Tissue also could be digested in addition with Trypsin (0.1 mg/ml) in EDTA-containing buffer for 10-60 min at temperatures 25-37° C., or with Collagenase, Dispase, DNA-se. Tissue could be wortexed, cells could be further isolated from debris and undigested tissue by filtering through 30-300 μ-pore filter, re-suspended in growth medium (GM). As growth medium, a variety of medium for cell growth known to those skilled in arts could be used. For example, MEM, DMEM, F12, RPMI-1640, alpha-MEM with or without 0.5-2.5 mM L-glutamine, and with or without fetal bovine serum (FBS), with or without antibiotics like penicillin/streptomycin or others alike. A variety of additional growth factors and supplements, for example EGF, HGF, VEGF, FGF and others could be used as supplements for plastic-adherent growth or three-dimensional growth on different substrates known to those skilled in arts.

Figure 1:
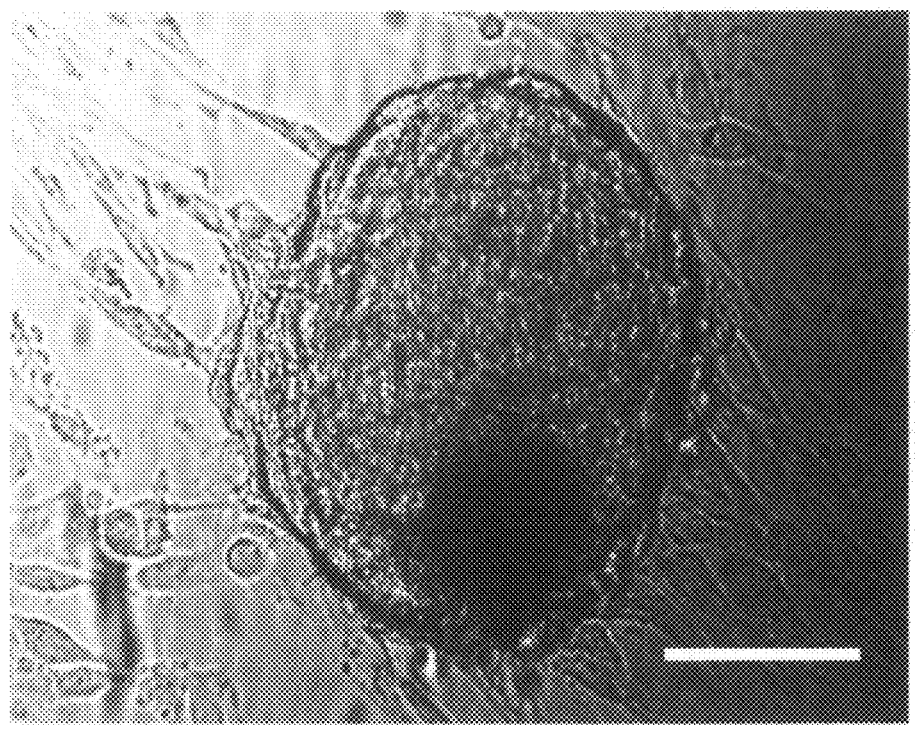
FIG. 1. Three-dimentional CCFUC spherical structure grown without plastic adherence from chorionic colony-forming cell units. Phase-contrast image. Bar is 150 μm.

To obtain colony-forming unit cells primary cultures are performed on plastic, semisolid support, or on feeder layers to assure growth of 3-dimentional spheroids, comprising colonies of colony-forming unit cells not attached to plastic. These spheroid colonies are collected by any means known to those skilled in art and further propagated in undifferentiated or differentiated state. Example of such spheroid non-adherent culture is shown in FIG. 1.

For further propagation, subconfluent or confluent primary cultures on plastic, semisolid support, feeder layers or three-dimensional structure support could be washed with PBS without $Ca^{++}$ $Mg^{++}$ (Invitrogen). Cells could be detached following Trypsin/EDTA or collagenase treatment of mechanical scraping. Cells could be re-suspended in GM and cultured in different size and brands of cell culture flasks, or culture dishes. Cells may have different morphology at this point, doubling time ranging from 12 to 72 hours. Further passaging allows obtaining homogenous cell population with doubling time 24-48 hours. Cells could be propagated over 70 doublings at plating efficiency $0.5\text{-}5\times10^4$ per $cm^2$.

Cells could express a variety of stem cell markers at various passages, which could be determined by immunostaining or RT-PCR. Examples of such stem cell markers include, but are not limited to: Nanog, CD-90, Oct-4, GDF-3(Growth differentiation factor 3), GABRB-3 (GABA receptor), SSEA-3, SSEA-4 (stage specific expression antigen), TRA-1-60 (tumor resistance antigen), FGF-4 (Fibroblast growth factor). Examples of expression of these stem cells markers are shown in Example 1.

Specifically, cells of current invention express protein ACBD6.

Cells are characterized by rapid growth with doubling time 24-48 hours, capability to form 3-dimentional structures not attached to substrate, but not capable of spontaneous differentiation into lineages of 3 germ layers, which distinguishes them from embryonic stem cells, embryobodies or "embryobody"-like formations.

These cells could be differentiated into different lineages, but only in specific differentiation media condition. For studies of differentiation potential, single clones (further termed clonally-derived CCFUC) were obtained by limiting dilutions method in semisolid mediums. Single clones were isolated, propagated and used in differentiation assays and for transplantation. For differentiation assays (Example 2) chorionic clonally-derived CCFUC could be cultured at initial concentration of $2\times10^5$ ml in GM in 60 mm Petri dishes. Adipogenic differentiation could be stimulated by seeding the cells for 3 weeks in GM supplemented with $10^{-6}$ mg/ml dexamethasone and 5 μg/ml insulin or by other means known to those skilled in arts. Osteogenic differentiation could be induced by culturing in GM containing 10 mM β-glycerol phosphate, 50 μg/ml ascorbic acid, and $10^{-6}$ mg/ml dexamethasone for 3 weeks or by other means known to those skilled in arts. Neurogenic differentiation could be performed by addition of retinoic acid ($10^{-7}\text{-}10^{-8}$ M to the medium) or NGF/EGF or by other means known to those skilled in arts.

Differentiation of clonally-derived cells of current invention into lung epithelial cells (endoderm) could be induced by culture in lung epithelial cell-specific media, for example by adding a set of hormones and growth factors consisiting of 1:1 mix of Dulbecco's Modified Eagle (DME) medium H-21 and Hank's F-12 mix supplemented with 15% (v/v) heat-inactivated FCS and the following growth factors: EGF (10 ng/ml), insulin (5 μg/ml), triiodothyronine (30 nM), transferrin (5 μg/ml), adenine (180 μM), epinephrine (5.5 μM), hydrocortisone (1 μM). Another way of directing differentiation of chorionic mesenchymal stem cells towards lung epithelial lineages is performing their co-culture without direct cell-to-cell contact with other epithelial cell lines of lung epithelium (for example A549, Calu-3, JEM) with or without presence of $Li^{++}$ (5-20 mM), as described in Example 2.

Differentiation of clonally-derived chorionic colony-forming unit cells into endothelial cells could be achieved by a variety of means, for example by culturing them in semi-solid media, of which Matrigel® is one example, in the presence of EGF, VEGF or other growth factors.

Cells of current invention could further be characterized by ability to propagate over 70 doublings in culture, demonstrating little changes in telomere length but at the same time having low telomerase activity. Telomerase activity could be measured by a variety of means, known to those skilled in arts, for example telomerase detection kit from Chemicon, according to manufacturer's protocol, as illustrated by Example 3.

Chorionic colony-forming unit cells could further be characterized by their ability to form three-dimensional structures, similar to "blasts" of hematopoietic colony-forming units. These structures are different from "embryobodies" or "embryobody"—like structures, as cells in these structures do not undergo spontaneous differentiation into lineages of three germ layers. Formation of three-dimensional structures occurs spontaneously in primary tissue digest or mechanically minced tissue. Induction of such structure formation in secondary and higher passages could also be achieved, for example by gentle trypsinization and mechanical removal to achieve cell precipitates, as illustrated in Example 1. The precipitates, or clusters of these cells, could be cultured in suspension in different media, for example in a medium consisting of 79% DMEM, 20% FBS, 2 mM L-glutamine, 1% MEM non-essential amino acids, and 0.1 mM β-mercaptoethanol. For differentiation analyses, cells could be plated onto a tissue culture dishes for immunostaining or RT-PCR analysis. Chorionic colony-forming unit cells could further be characterized by unaltered karyotype. Analyses of karyotype could be performed by a variety of methods well known to those skilled in arts, for example by treatment of cultures with 0.1 μg/ml colcemid (Gibco BRL) for 3 hours, incubation in hypo-tonic solution at 37° C. for 30 minutes in a 5% $CO_2$ atmosphere, fixation in methanol:glacial acetic acid (3:1) three times, and placement onto chilled glass slides.

Chorionic colony-forming unit cells could further be characterized by release of abundant amounts of multiple growth factors and cytokines, for example FGF, KGF, HGF, angiopoietins 1, SCF, VEGF, G-CSF, NGF and others.

Clonally-derived chorionic colony-forming unit cells could further be characterized by their ability to graft humans or immunocompromised animals, i.e. to form so-called "chimeras", as illustrated in Example 4. In animals, a standard approach is to use sub-lethally or lethally irradiated mice of multiple strains. For example, after 4-10 passages on feeder-layers, $10^6$ colony-forming unit cells could be injected into the leg muscle of NOD/SCID mice, or these cells could be injected IP into 2.5-3 Gy irradiated NOD/SCID mice. Engraftment of colony-forming unit cells into different organs of mice and their differentiation into different tissue and organ-specific phenotype could be determined following 10-12 weeks. To determine engraftment and differentiation, a variety of different means known to those skilled in art could be used, for example, tissue immunostaining, in situ-hybridization for human-specific chromosomes, RT-PCR and other, as illustrated in Example 4.

Chorionic colony-forming unit cells could further be characterized by their ability to graft humans. Autologous or allogeneic colony-forming unit cells could be introduced into the body of a human recipient by a variety of means with therapeutic purposes. To determine engraftment and differentiation, a variety of different means known to those skilled in art could be used, for example, immunostaining of biopsy specimen, in situ-hybridization for donor-specific DNA, RT-PCR and other.

3. Primary Colony-Forming Unit Cells Isolated from Chorion of Placenta (PCCFUC).

Cells may be also isolated from tissue of chorion by a variety of methods based upon expression of surface marker ACBD6 as a first step and as a second step based upon expression of markers of human pluripotent stem cells: TRA-1-60, SSEA-3, SSEA-4 or combination of these factors as illustrated in Example 5. Different methods known to those skilled in art include but not limited to using magnetic beads with absorbed antibodies to surface molecules, immuno-absorption on different carriers, Fluorescent—assisted cell sorting (FACS). FACSorting could be performed based upon expression of different surface antigens. Following FACsorting, this fraction of cells could be cultured in conditions required to maintain human ESC in undifferentiated state on feeder layers, as tested by their ability to propagate above 50 doublings in culture, expression of embryonic stem cell-specific markers, engraftment of NOD/SCID mice, no expression of telomerase, formation of three-dimensional structures without spontaneous differentiation, normal karyotype and ability to further differentiate into different lineages of all germ layers only in specific differentiation media.

Mouse embryonic fibroblast feeder layers are usually used to culture human embryonic stem cells, though it makes these cells un-suitable for purpose of therapy in humans. Other culture systems for human embryonic stem cells include embryonic and skin fibroblasts, bone marrow MSC. These, as well as other types of feeder layers from a different origin could be used for propagation of CCFUC.

Feeder layer derived from colony-forming unit cells could be grown on solid support. For example, serum-free culture medium for CCFUC could be used with the following formulation: 79% (DMEM)/F-12 supplemented with 20% knock-out serum replacement (SR), 2 mM L-glutamine, 1% minimal essential medium (MEM)—nonessential amino acid solution, 0.1 mM β-mercaptoethanol, and 4 ng/ml human recombinant bFGF.

Colony-forming unit cells could express a variety of stem cell markers at various passages, which could be determined by immunostaining or RT-PCR. Examples of such stem cell markers include, but are not limited to: Nanog, CD-90, GDF-3 (Growth differentiation factor 3), Oct-4, SSEA-3, SSEA-4, TRA-1-60 (tumor resistance antigen), FGF-4 (Fibroblast growth factor). Examples of expression of some of these stem cells markers are shown in Example 1.

Novel stem cell markers for CCFUC include ACBD6. Expression of ACBD6 by placental stem cells was described by inventors (Soupene et al, 2008).

This description demonstrates that claimed chorionic colony-forming unit cells are different from earlier described or claimed lines of hAEC, hAMSC, hCMSC by several new and important features: 1. Cells propagate over 50 doublings, while cell lines obtained from amniotic membrane and amniotic mesenchyme did not propagate over 30 doublings; 2. Clonally-derived cells could be differentiated into neuron-like cells (ectoderm), adipocytes, osteoblasts (mesoderm), hepatocytes and lung epithelial cells (endoderm)—derivatives of all three germ layers; 3. Colony-forming unit cells from placental chorionic tissue form three dimensional spherical structures; 4. CCFUC express multiple growth factors, including HGF, FGF-beta, angiopoietins; 5. Cells express markers ACBD6 as well as markers of pluripotent stem cells Oct-4, Nanog, SSEA-3.

Claimed novel colony-forming unit cells with high yield and paracrine properties are favorable for tissue repair. Large volume of chorionic mesoderm provides very large source of these cells from single placenta (total estimate $10^8$-$10^9$ cells per placenta).

4. Utility: Therapeutic Use of Colony-Forming Unit Cells from Placental Chorion and Their Products.

Pharmaceutical compositions comprising stem cells or their derivatives could be administered to a human using multiple cells culture carriers well known to those skilled in arts. Composition depends upon the target organ and route of administration. Cells could be delivered systemically, via artery or vein, or locally, using instillation into a wound, airways, application to the skin or infusion or injections into tissues by means of catheter or needle. Carriers could be chosen from a variety of media solutions used for cell culture.

Clinical applications of the collected cells include treatment of a disorder in an individual (e.g., a human) from whom the fetal stem/progenitor cells were obtained. For example, collected stem/progenitor cells, or progeny thereof, can be introduced into an individual in need thereof, to treat a condition or disorder. The individual can be a neonate (e.g., an individual in an age range of from about one week to about one month), an infant (e.g., an individual in an age range of from about one month to about 12 months), a toddler (e.g., an individual in an age range of from about 12 months to about 3 years), a child in an age range of from about 3 years to about 8 years, a pre-teenager (e.g., an individual in an age range of from about 9 years to about 12 years), a teenager (e.g., an individual in an age range of from about 13 years to about 19 years), an adult (e.g., an individual 20 years old or older), a geriatric patient (e.g., an individual in an age range of from about 65 years to 100 years or older); etc.

Collected stem/progenitor cells, or progeny thereof, can be used to provide tissues for grafting such as bone marrow, skin, cartilage, tendons, bone, muscle (including cardiac muscle), blood vessels, cornea, neural cells, gastrointestinal cells, etc.

Myocardial ischemia is a condition characterized by restriction of blood supply to the heart. Causes of myocardial ischemia are mostly related to diseases of blood vessels, resulting in damage to the heart tissue, which could be myocardial infarction, sclerosis or fibrosis. Ischemia leads to tissue damage because of lack of oxygen and nutrients and a build-up of metabolic wastes. Ischemia can also be caused by blockade or constriction of the blood vessels. Causes of myocardial tissue ischemia are atherosclerosis, embolism, and hypertension. Myocardial infarction is the process of tissue death (necrosis) caused by ischemia. Infarctions of heart are commonly associated with hypertension, thrombosis or atherosclerosis. Conservative treatment includes smoking cessation, exercise, medication with anticoagulants, vasodilators and statins. Surgical treatments include angioplasty on coronary arteries, placement of a stent.

Cell lines of colony-forming unit cells from placental chorion and their products, as well as primary cells of current invention may be used for the purpose of treatment of ischemic lesions in myocardial ischemic diseases due to their ability to facilitate formation of vessels and enhance regeneration of tissue by stimulating cell proliferation as illustrated in detail in Example 6. Introduction of stem cell lines described by this invention at the dose $5\text{-}50\times10^6$ cells at the site of ischemic lesions in myocardial infarction results in enhanced rate of new capillaries formation and enlargement of existing arteries, as illustrated in detail in Example 6. This restoration occurs due to a massive and balanced release by the cells of current invention of multiple growth factors, including but not limited to angiopoietin-1, HGF, FGF, KGF, VEGF, GM-CSF.

Spinal cord injuries is the damage to fiber tracts in spinal cord that carry signals to and from the brain. Traumatic injury could also damage the gray matter in the central part of the cord formed by neuronal bodies, which results in segmental losses of interneurons and motorneurons. Spinal cord injury can occur from many causes, including trauma, tumors, occlusion of spinal blood vessels, inflammation. In a case when spinal cord is completely cut, function below the level of injury is lost, which manifests in absence of motor and sensory function. Less than 5% of people with "complete" spinal cord injuries recover locomotion. In an "incomplete" injury, some sensation and/or movement below the level of the injury remains. Multiple therapeutic approaches are aimed at reducing the paralyzing effects of injury and promoting regrowth of functional nerve fibers. Stem cell-based therapies utilizing bone marrow-derived cells are among them. However, results of such treatments reported in literature still are not satisfactory. This is a subject matter of current invention to provide a method of treatment of spinal cord and other types of injuries to nerves by administering the placental-derived colony-forming unit cells of current invention.

Cell lines of colony-forming unit cells from placental chorion and their products, as well as primary cells of current invention may be used for the purpose of treatment of spinal cord injuries, peripheral nerve lesions, other neurological diseases associated with neuro-dystrophy due to their ability to facilitate formation of vessels and enhance regeneration of tissue by stimulating cell proliferation as illustrated in detail in Example 7. Introduction of stem cell lines described by this invention at the dose $5\text{-}50\times10^6$ cells at the site of nerve lesions results in enhanced rate of nerve tissue regeneration, as illustrated in detail in Example 7. This restoration occurs due to a massive and balanced release by the cells of current invention of multiple growth factors, including but not limited to angiopoietin-1, HGF, FGF, KGF, VEGF, GM-CSF.

There are many similarities in clinical manufestation between spinal cord injuries and other types of neurodegenerative and muscular degenerative diseases, all resulting in loss of muscle motor activity. Multiple diseases of muscle fibers are generally termed "muscular dystrophy". This group of diseases is characterized by progressive striated muscle weakness, defects in expression of key proteins of myocytes, and apoptosis of myocytes. Diseases include Duchenne, Becker, limb girdle, congenital, facioscapulohumeral, myotonic, oculopharyngeal, distal, and Emery-Dreifuss syndromes, though there are more than 100 diseases similar to muscular dystrophy. Most types of myodystrophy are multisystem disorders with manifestations in body systems. Stem cell-based therapy is a new potential approach for the treatment of chronic degenerative muscular diseases. The effects of transplanted stem cells on muscle recovery may not necessarily be due to transformation, transdifferentiation or fusion with existing myocytes. The release of paracrine mediators by transplanted stem cells facilitates the recovery of striated myocytes. Previous reports have described the use of myoblast transplantation to rescue muscles in muscular dystrophy. The drawback of this approach is that myoblasts show a very low level of survival after injection. When stem cells from the bone marrow are transplanted in the dystrophin deficient (mdx) mouse, donor cell-derived dystrophin could be detected in affected muscle fibers. However, in general, the contribution of donor cells to affected muscle is low and did not improve the muscle function. The low frequency event of transformation of bone-marrow-derived cells may represent transdifferentiation of marrow stem cells into muscle or fusion events. Previous approaches using transplantation of myocytes, bone marrow-derived stem cells did not demonstrate sufficient efficacy of these procedures. As of now, there is no known cure for muscular dystrophy. Therefore, this is a subject matter of current invention to provide a method for treatment of muscular dystrophy syndromes by administering the placental-derived colony-forming unit cells of current invention.

Cell lines of colony-forming unit cells from placental chorion and their products, as well as primary cells of current invention may be used for the purpose of treatment of muscular dystrophy syndromes due to their ability to facilitate formation of vessels and enhance regeneration of tissue by stimulating cell proliferation as illustrated in detail in Example 8. Introduction of stem cell lines described by this invention at the dose 5-50×10$^6$ cells at the site of nerve lesions results in enhanced rate of nerve tissue regeneration, as illustrated in detail in Example 8. This restoration occurs due to a massive and balanced release by the cells of current invention of multiple growth factors, including but not limited to angiopoietin-1, HGF, FGF, KGF, VEGF, GM-CSF.

Examples

Culture Characteristics of Chorionic Colony-Forming Unit Cells

Example 1

Chorionic colony-forming unit cells were derived from human term placenta. Following IRB approval and informed consent, placentas were obtained from healthy females following caesarian section. Freshly obtained human placentas, some of which have been subjected to a conventional cord blood recovery process by draining substantially all of the cord blood from the placenta were used. Placentas were first infused with an anticoagulant/vasodilator solution (Heparin 30 U/ml, papaverin 0.05 mg/ml) at a temperature of 20° C. For perfusion procedures, artery and vein of umbilical cord were further cannulated and connected to a perfusion circuit, which contained heat exchange unit, blood oxygenator, roller pump and perfusion reservoir. Blood oxygen tension and carbon dioxide tension, temperature of perfusate and perfusate flow rate were continuously monitored. Pressure in the umbilical cord artery and vein was constantly measured using Baxter pressure transducers connected to blood pressure monitor (Protocol Systems, Portland, Oreg.). Constant temperature of perfusate was maintained using heat exchange unit connected to temperature-controlled water bath. Perfusate after several hours of perfusion was collected, and cells obtained from perfusate were designated as PDPSC.

Amnion and amniotic mesenchyme were isolated from chorion. Chorionic tissue was minced and cells were isolated by filtration through 400 micron filter, than 100 micron filter and placed in culture medium: alpha-Modified Eagle's Medium (MEM) with PSF, 15% fetal calf serum (FCS), 2 mM L-glutamine. Sample of obtained cell suspensions were stored at 4° C. for fluorescence activated cell sorting (FACS) analyses.

Figure 2A:
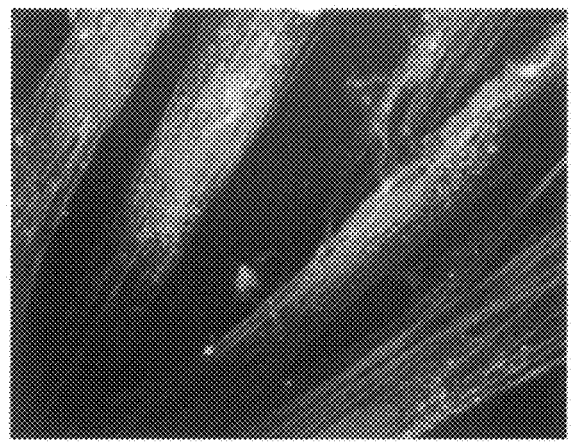
FIG. 2. Phenotype of cell cultures of chorionic colony-forming unit cells. Colony-forming cell units from placental chorion expressed markers of pluripotent stem cells. Fluorescent immunostaining (merged images) showing staining for A: TRA-1-60, FITC-green, nuclei—DAPI(blue); B: Western blot staining for Oct-4 and NANOG in 4 lines of clonally-derived placental cell lines. Positive control—embryocarcinoma cell line NTRA-2, negative control—human fibroblasts (IMR90).
Figure 2B:
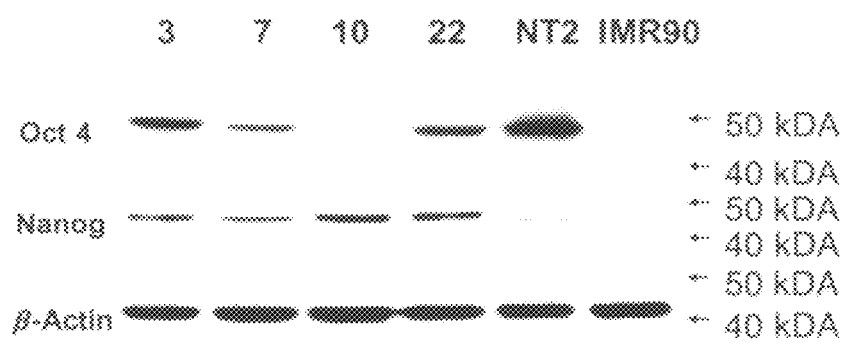

To further isolate colony-forming unit cells non-adherent to plastic, following treatment with cell-liberating compositions, tissue was gently wortexed, cells were further isolated from debris and filtered through 70 µ-pore filter, re-suspended in growth medium (GM): alpha-MEM with 2 mM L-glutamine, and with 10% of fetal bovine serum (FBS, HyClone), with antibiotics penicillin/streptomycin and cultured at 37° C. in atmosphere of 5% $CO_2$ and 95% air. Cell suspension was placed in 24-well cluster at dilutions 1:2, 1:10, 1:50; 1:100. After 10-14 days of culture with addition of 0.2 ml of fresh medium every 3-4 days, colonies of attached and non-attached cells were identified, and single colonies were isolated as shown in FIG. 1. Clonally-derived colony-forming unit cells were isolated from three-dimensional spherical structures of growing cells, not attached to substrate. For further propagation, primary cultures were washed with PBS without $Ca^{++}$ $Mg^{++}$ (Invitrogen). Cells were detached from each other following Trypsin/EDTA treatment or mechanical scraping. Though initial cell cultures were isolated as non-attached to substrate cell clones, further propagation was performed in substrate-attached cultures. Phenotype of these cultures is shown in FIG. 2. Subsequent two passages were performed as cells became confluent, by splitting the cells at 1:2 ratio. Further passages produced homogenous cell population with doubling time 24-28 hours. Twenty cell lines were propagated over 100 doublings at plating efficiency 0.5-2.5×10$^4$ per cm$^2$ by splitting cells at 1:4 ratio in alpha-MEM with 2 mM L-glutamine and 10% of fetal bovine serum (FBS) (Invitrogen) without penicylline/streptomycin.

Cells of amniotic membrane and mesenchyme (AMSC), and perfusion-derived cells (by the method described by Hariri (U.S. Pat. No. 7,045,148; U.S. Pat. No. 7,311,905; U.S. Pat. No. 7,468,276; U.S. Pat. No. 7,498,171) were derived similarly and used for comparison for gene expression analyses.

Figure 3:
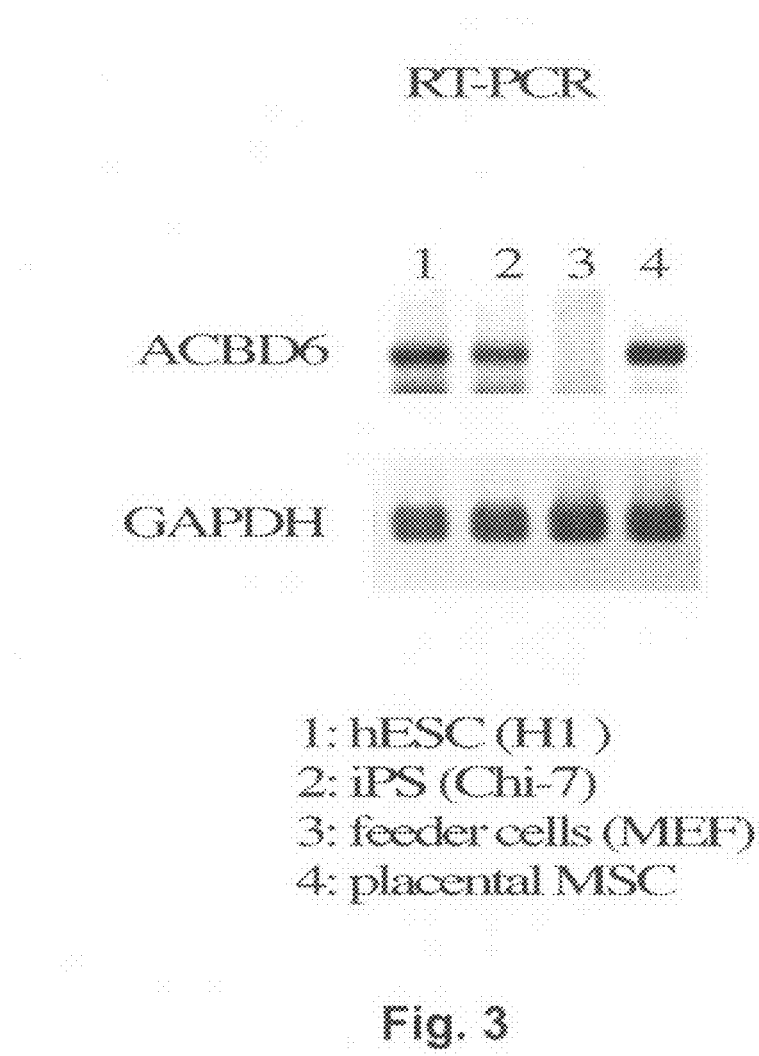
FIG. 3. Expression of ACBD6 protein by RT-PCR in placental cells of current invention. Positive control—human embryonic stem cell line H1 (hESC H1); induced pluripotent stem cells (iPC Chi-7); negative control—feeder cells (MEF). Housekeeping gene expression shown by GAPDH.

Cells expressed a variety of stem cell markers at various passages, which could be determined by RT-PCR: Nanog, CD-90, GABRB-3 (GABA receptor), Oct-4, SSEA-3, SSEA-4 (stage specific expression antigen), FGF-4 (Fibroblast growth factor). Expression of stem cell markers TRA-1-60, Nanog, and Oct-4 is illustrated in FIG. 2. Other cells used for comparison: bone marrow MSC (BMMSC), fibroblasts, and obtained by placental perfusion as described by Hariri (U.S. Pat. No. 7,045,148; U.S. Pat. No. 7,311,905; U.S. Pat. No. 7,468,276; U.S. Pat. No. 7,498,171) did not express Nanog, SSEA-3, Neurofilament-200, ACBD6. Expression of ACBD6 is illustrated in FIG. 3.

Gene expression analysis was done by real time quantitative TaqMan PCR systems. For each target gene, pre-developed TaqMan PCR assays (Assay-on-Demand) were purchased from Applied Biosystems (Foster City, Calif.). Cells were immediately placed into 500 microliter of 1× AB lysis buffer (Applied Biosystems), incubated at room temperature for 30 min and then total RNA (tRNA) extracted. Proteinase K and two grinding beads (4 mm diameter, stainless steel beads, SpexCertiprep, Metuchen, N.J.) were added and the tissues homogenized in a GenoGrinder2000 (SpexCertiprep) for 2 min at 1000 strokes per minutes. Protein digest was done at 56° C. for 30 min and followed by a 30 min period at −20° C. to reduce foam and precipitate RNA. Total RNA was extracted from the tissue lysates using a 6700 automated nucleic acid workstation (Applied Biosystems) according to the manufacturer's instructions. Complementary DNA (cDNA) was synthesized using 100 units of SuperScript III (Life Technologies), 600 ng random hexadeoxyribonucleotide (pd(N)$_6$) primers (random hexamer primer) 10 U RNaseOut (RNase inhibitor), and 1 mM dNTPs (all Invitrogen, Carlsbad, Calif.) in a final volume of 40 µl. The reverse transcription reaction was done for 120 min at 50° C. Samples were run in 96 or 384 well plates in an automated fluorometer (ABI PRISM 7900 HT A FAST, Applied Biosystems). AB's standard amplification conditions were used: 2 min at 50° C., 10 min at 95° C., 40 cycles of 15 s at 95° C. and 60 s at 60° C. Fluorescent signals were collecte during the annealing temperature and CT values extracted with a threshold of 0.04 and baseline values of 3-15. In order to determine the most stably transcribed housekeeping gene, a housekeeping gene validation experiment was conducted on a representative number of samples from all tissue types. At least 6 commonly used housekeeping genes were be used for this experiment: a TaqMan PCR system recognizing 18S rRNA (ssrRNA), GAPDH HPRT1, TFR2, RPLPO and B2M. The housekeeping gene with the least standard deviation in all treatment groups were used to normalize the target gene CT values. Final quantification was done using the comparative CT method (User Bulletin #2, Applied BioSystems) and reported as relative transcription or the n-fold difference relative to a calibrator cDNA (i.e. lowest target gene transcription). The housekeeping gene was used to normalize the CT values of the target genes (ACT). The linear amount of target molecules relative to the calibrator was calculated by $2^{-\Delta\Delta Ct}$. All gene transcriptions were expressed as an n-fold difference relative to the calibrator. Results for chorionic mesenchymal-derived lines 1C, 2C, 3C and amniotic mesenchymal derived lines AMSC were normalized to expression of the gene of interest (normalized toward housekeeping gene) relatively human embryonic fibroblasts (negative control) and are shown in Table 1.

Summary of phenotype characteristics of ESC, placental-derived stem cells: amniotic (AMSC), perfusion-derived (as described by Hariri, U.S. Pat. No. 7,045,148; U.S. Pat. No. 7,311,905; U.S. Pat. No. 7,468,276; U.S. Pat. No. 7,498,171) and CCFUC or current invention is given in Table 2.

TABLE 1

Gene expression profile in different clones of chorionic colony-forming unit cell (1C, 2C, 3C) and amniotic mesenchymal stem cells.

| Line # | Nanog | OCT-4 | SSEA-3 | GABR-B3 |
|---|---|---|---|---|
| 1C | 12 ± 4 | 4 ± 1 | 4 ± 2 | 2 ± 1 |
| 2C | 25 ± 6 | 3 ± 1 | 5 ± 1 | 5 ± 2 |
| 3C | 8 ± 5 | 7 ± 1 | 3 ± 1 | 11 ± 5 |
| AMSC | 13 ± 11 | 3 ± 2 | 2 ± 2 | 5 ± 2 |

Expression is normalized to the expression of most stable housekeeping gene (n-fold difference relative to calibrator). Relative expression as compared to expression of subsequent gene in human fibroblasts is given as MEAN ± SE.

TABLE 2

Summary of phenotype characteristics of ESC, placental-derived stem cells: amniotic (AMSC), perfusion -derived (as described by Hariri) and CCFUC.

| Phenotype | ESC | AMSC | Perfusion-derived placental SC | CCFUC |
|---|---|---|---|---|
| Oct-4 | + | + | + | + |
| SSEA-3 | + | + | − | + |
| TRA-1-60 | + | + | − | + |
| NANOG | + | + | − | + |
| Nestin | − | − | − | + |
| Neuro filament | − | − | − | + |
| CD90 | − | + | + | + |
| ACBD6 | + | +/− | − | + |
| HGF Secretion | − | +/− | − | + |
| KGF Secretion | − | +/− | − | + |
| Ang-1 Secretion | − | − | − | + |
| Differentiation in lineages | 3 | 3 | 1 | 3 |
| Sphere Formation | + | − | + | + |
| Plastic Adherence | − | + | + | + (−) |
| Teratoma formation | + | + | − | − |
| Number of Doublings | >250 | 20 | 20 | 70 |
| Teromerase Activity | high | | | Low |
| Telomere Length | Maintained | | | Maintained |

Example 2

Three-dimensional spherical structures (FIG. 1) grown as free-standing or free-floating structures or attached in part to solid support did not demonstrate differentiation into lineages of 3 germ layers under standard culture conditions. This is important distinction of these culture forms of chorionic colony-forming unit cells from embryonic cells, embryobodies or "embryobody-like" structures.

Figure 4:
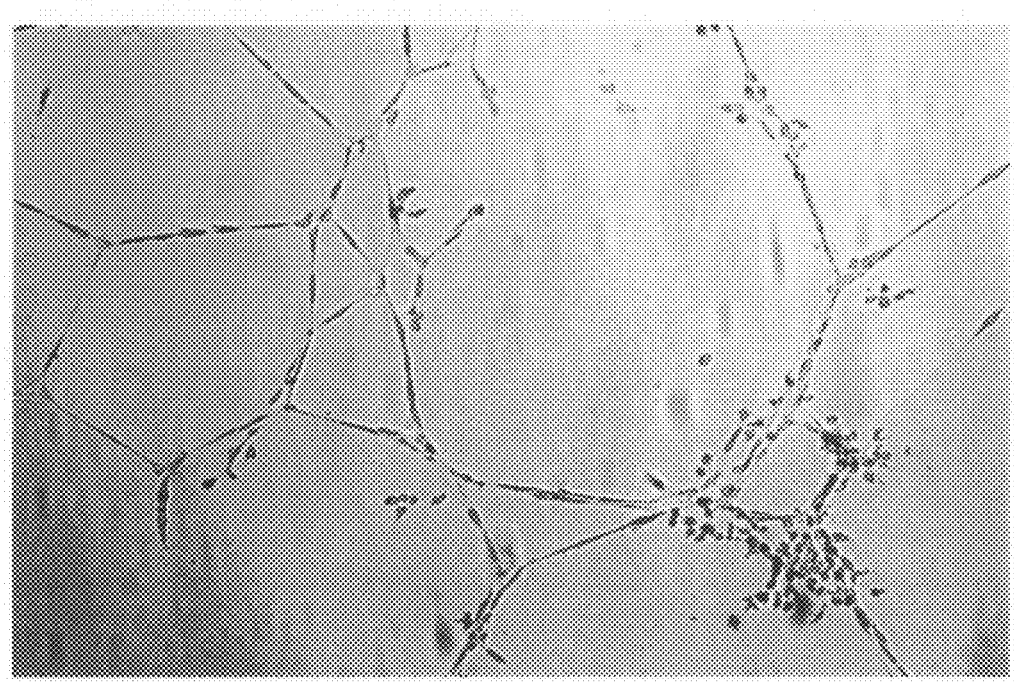
FIG. 4. Examples of in vitro differentiation of chorionic colony-forming unit cells into vascular endothelial cells. Cell culture of chorionic colony-forming unit cell grown on Matrigel®, typical vascular capillary structure formation. Phase-contrast vital microscopy, magnification ×10.

For directed differentiation assays chorionic clonally-derived colony-forming unit cells were grown in GM in Petri dishes, containing sterile pieces of cover glass. Adipogenic differentiation (mesoderm) was stimulated by seeding the cells for 3 weeks in GM supplemented with $10^{-6}$ mg/ml dexamethasone and 5 µg/ml insulin. Osteogenic differentiation (mesoderm) was induced by culturing in GM containing 10 mM β-glycerol phosphate, 50 µg/ml ascorbic acid, and $10^{-6}$ mg/ml dexamethasone for 3 weeks. Differentiation into vascular endothelial cells and blood cells (mesoderm) was performed by culturing chorionic colony-forming unit cells either on 50% Matrigel® (BD Biosciences)/50% serum—coated wells, or in semi-solid medium Methocult® (Stem Cell technologies, Vancouver, Canada). Following culture in adipogenic differentiation medium, cell cultures demonstrated presence of lipid vacuoles as revealed by Oil Red staining, indicative of adipogenic differentiation. Following culture in osteogenic differentiation medium, cell cultures demonstrated presence of calcium precipitates as revealed by Alizarin Red staining, indicative of osteoblast differentiation. Following 2-week culture in Methocult® chorionic colony-forming unit cells expressed endothelial cell markers CD31 and VEGFR2 (KDR), and formed tubular capillary network, as illustrated in FIG. 4 for substrate-adherent cell.

Figure 5:
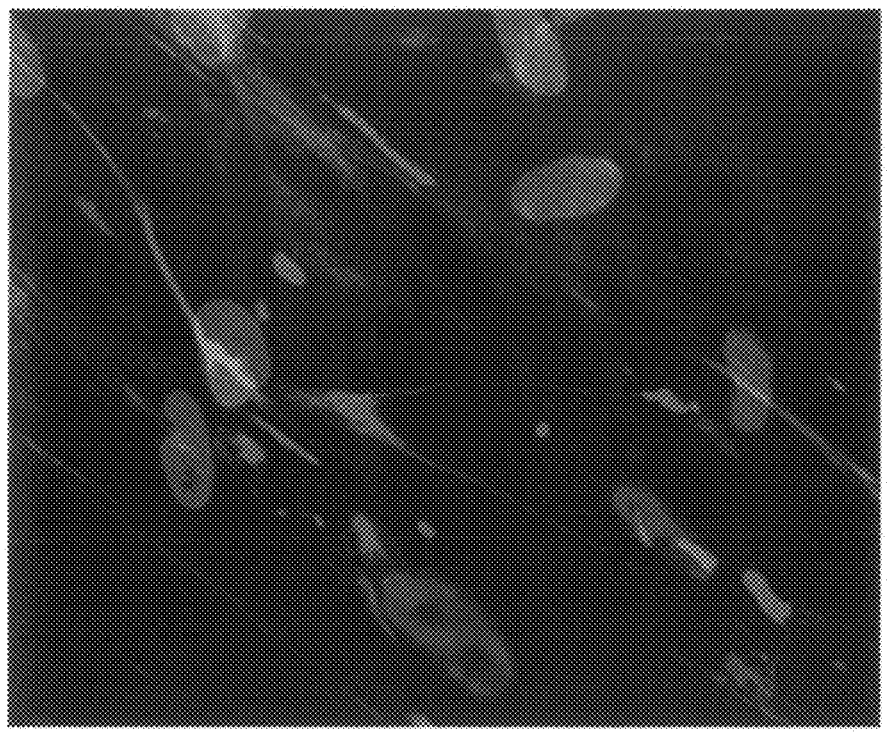
FIG. 5: Colony-forming cell units from placental chorion expressed markers of neurons upon culture in medium with NGF. Fluorescent immunostaining (merged images) showing staining for neuronal marker Nestin (Green, FITC, nuclei DAPI-blue).

Neurogenic differentiation (ectoderm) was done by addition of retinoic acid ($5 \times 10^{-8}$ M to the medium) and $10^{-8}$ M NGF. Following culture in retinoic acid and culture in the presence of $10^{-8}$ M NGF in the medium, cell cultures demonstrated morphology characteristic of human neurons, expression of neurofilament-200, nestin (illustrated in FIG. 5), acetylcholine receptor, MusKinase, agrin, all of which are markers of neuronal differentiation. Perfusion-derived cells (PDPSC) did not show this type of differentiation.

Differentiation of chorionic clonally-derived colony-forming unit cells into lung epithelial cells was induced by culture in lung epithelial cell-specific media by addition a set of hormones and growth factors (further called Airway Epithelium Differentiation Medium-AEDM) consisting of: a 1:1 mix of Dulbecco's Modified Eagle (DME) medium H-21 and Hank's F-12 mix supplemented with 15% (v/v) heat-inactivated FCS (Life Technologies) and the following growth factors: EGF (10 ng/ml), insulin (5 µg/ml), triiodothyronine (30 nM), transferrin (5 µg/ml), adenine (180 µM), epinephrine (5.5 µM), hydrocortisone (1 µM). In another experiment, differentiation of chorionic mesenchymal stem cells towards lung epithelial lineages was done by co-culture without direct cell-to-cell contact with another lung epithelial cell line A549. Gene expression analyses as shown in Table 3, demonstrated multi-fold increase in expression of genes characteristic of lung epithelial cells: Cytokeratins 5, 8, 4, ZO-1, surfactant protein and mucin, all indicative of differentiation into endodermal lineages of lung epithelial cells. Perfusion-derived cells (PDPSC) did not show this type of differentiation.

TABLE 3

Gene expression profile in chorionic mesenchymal stem cell lines following differentiation into lung epithelial cells.

| Gene | Control Medium | AEDM | Coculture With A549 |
|---|---|---|---|
| Cytokeratin 5 | 0.1 ± 0.1 | 0.6 ± 0.2* | 1.02 ± 0.3* |
| Cytokeratin 8 | 0.2 ± 0.1 | 2.0 ± 052* | 1.2 ± 0.4* |
| Cytokeratin 14 | 0.1 ± 0.2 | 0.7 ± 0.1* | 1.2 ± 0.5* |
| ZO-1 | 0.01 ± 0.01 | 0.15 ± 0.05* | 0.25 ± 0.2* |
| Surfactant Protein C | 0.01 ± 0.01 | 0.1 ± 0.1* | 0.05 ± 0.01* |
| Surfactant Protein A | 0.1 ± 0.1 | 0.3 ± 0.2* | 0.5 ± 0.2* |
| Mucin | 0.01 ± 0.01 | 0.12 ± 0.1* | 0.05 ± 0.01* |

Expression is normalized to the expression of most stable housekeeping gene. Relative expression is given as MEAN ± SE.

Chorionic cells were further differentiated in vitro into hepatocytes (endoderm) in culture medium containing 1000 ng/ml HGF and 50 ng/ml FGF. Following 3-week culture, cells started to express albumin, alfa-1-antitrypsin, alpha-fetoprotein, which was confirmed both by RT-PCR to these markers (more than 10-100 fold increase in expression) and by immunostaining. Perfusion-derived cells (PDPSC) did not show this type of differentiation.

Therefore, this example demonstrates that chorionic colony-forming unit cells do not undergo spontaneous differentiation in vitro under standard conditions. These cells could be directed to differentiate in vitro into lineages of all 3 germ layers: mesoderm—adipocytes, osteoblasts, endothelial cells; ectoderm—neurons; and endoderm—lung broncho-epithelial cells and hepatocytes.

Example 3

Figure 6:
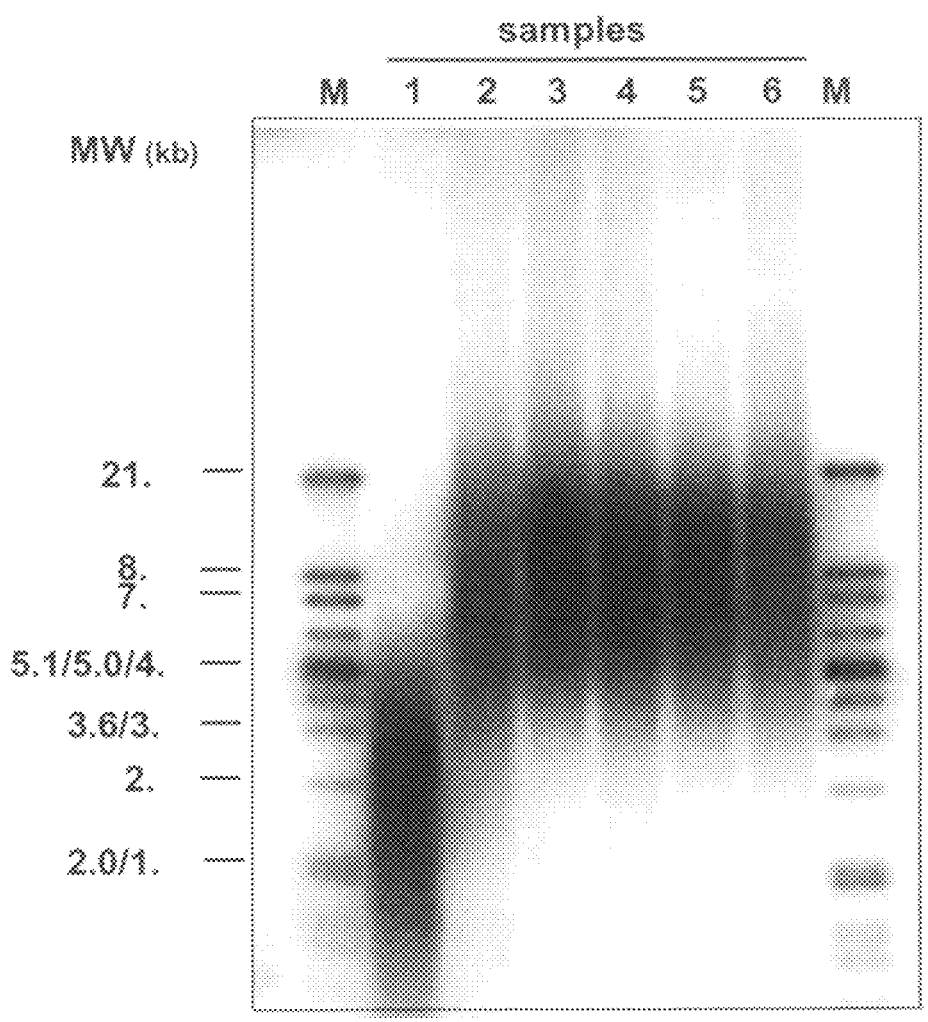
FIG. 6. Colony-forming unit cells of current invention maintain telomere length though passaging over 50 doublings. Telomeres length in early and late passages is not different. Samples: (1) Control DNA with low telomere length. (2) Control DNA with high telomere length. (3-6) Telomere length was unchanged in CCFUC cultures at late passages: (3) Line 3 passage 5; (4) Line 3 passage 55 (approximately 150 doublings); (5) Line 10 passage 8; (6) Line 10 passage 34 (approximately 100 doublings). (M) Molecular weight (MW) markers are displayed in kilobases (kb).

Chorionic colony-forming unit cells were characterized by absence of telomerase activity. Telomerase activity was measured by telomere repeat amplification protocol (TRAP) with the TRAPEZE telomerase detection kit Telomerase Detection Kit (S7700, Chemicon) according to the manufacturer's protocol. Briefly, $10^5$-$10^6$ cultured cells were lysed in 0.2 ml of Chaps buffer and 0.2-1 µg of cell extract protein was used TRAP assay. The extended and amplified TRAP products were resolved on 12.5% non-denaturing polyacrylamide gel. The relative telomerase activity was determined by the densitometric analysis of TRAP reaction products in relation to its telomerase quantitation control, 36-bp PCR amplification internal control and to the TRAP signals for telomerase positive standard cell extract. Telomere length was determined by terminal restriction fragment (TRF) analysis with the TeloTAGGG Telomere Length Assay Kit (Roche). Isolated genomic DNA (1-2 µmg) was digested with a Hinfl/Rsal enzyme mixture for 12-16 h at 37° C. Then, DNA samples were resolved by 0.6% agarose gel electrophoresis, gels were Southern blotted to a positively charged nylon membrane (Amersham, Hybond N+), which was then hybridized with a digoxigenin (DIG)-labeled probe specific for telomeric repeats and incubated with a DIG-specific antibody covalently coupled to alkaline phosphate. TRF lengths were estimated from a densitometric analysis of the Southern blot images, as illustrated in FIG. 6.

As compared to human embryonic adenocarcinoma cell line NTRA-2, telomerase activity of chorionic colony-forming unit cells was undetectable. However, chorionic colony-forming unit cells demonstrated no significant change in telomere length after more than 50 doublings. Normal karyotype was determined at over 50 doublings.

Chorionic colony-forming unit cells were characterized by release of abundant amounts of multiple growth factors and cytokines, such as FGF, KGF, HGF, angiopoietins and others, as illustrated in Table 4. Levels of these growth factors were measured by standard ELISA. Fibroblasts, ESC and perfusion-derived cells (PDPSC) did not show such profile of growth factor secretion.

TABLE 4

Growth factors determined in tissue growth medium following 96 hours of cell culture (pg/ml).

| Line | FGF-b | HGF | VEGF | Angiopoietin 1 |
|---|---|---|---|---|
| Fibroblasts | 2 ± 3 | 10 ± 3 | ND | ND |
| BM MSC | 25 ± 6 | 253 ± 35 | 64 ± 51 | 1230 ± 150 |
| CCFUC | 82 ± 12 | 1357 ± 150 | 780 ± 305 | 4860 ± 700 |
| AMSC | 23 ± 12 | 568 ± 124 | 512 ± 78 | 2380 ± 510 |
| PDPSC | 2 ± 1 | 40 ± 10 | 100 ± 23 | ND |

Human fetal fibroblasts and human bone marrow-derived cells are used as controls. Growth factors levels measured by ELISA, values are in pg/ml. BMMSC—bone marrow-derived human mesenchymal stem cells; CCFUC—colony-forming chorionic cells; AMSC—human amniotic mesenchymal stem cells, PDPSC—perfusion-derived placental stem cells.

Example 4

After 4-10 passages of cells from male donors, $10^6$ chorionic colony-forming unit cells were injected IP and subcutaneously into 12 2.5Gy-irradiated NOD/SCID mice. Engraftment of CCFUC into different organs of mice and their differentiation into different tissue and organ-specific phenotype was determined following 3-9 months by PCR for human beta-globin gene, immuno-staining for human CD45 and HLA-DR, and fluorescent in situ hybridization (FISH) for human Y-chromosome. For PCR, DNA was isolated using standard DNA isolation kits from Invitrogen, and PCR was performed using standard procedures and kits (Invitrogen). Results demonstrated presence of human beta-globin gene in almost all organs of chimeric mouse 6 months after transplantation of chorionic colony-forming unit cells (FIG. 7).

Tissues harvested from NOD/SCID animals were fixed in paraformaldehype, embedded in paraffin, cut, and used for immunostaining, FISH or both. Tissue slices were deparaffinized in Xylenes, washed in PBS, permeabilized with cold Methanol (−20° C.) and 1% Triton X-100 for 5 min. Slices were incubated with blocking buffer (3% BSA in 4×SCC, 2% goat serum, 3% FCS, 0.1% Tween 20) for 60 min at 37° C. and incubated with primary antibody (1:100 dilution) overnight at 4° C. Slices were washed, incubated with blocking solution for 20 min and then incubated with secondary Ab (1:500) labeled with FITC- or Alexa Fluor-633 for 60 min at 37° C., washed, mounted on slides with Gold Antifade reagent (Molecular probes, Eugene, Oreg.). To determine the presence of human Y-chromosome, Y-chromosome paint from Cambio Ltd. (UK) was used according to manufacturer's protocol. FISH was combined with staining for Cytokeratins 18 and 20 (intestine), cytokeratins 18, 20, Pancytopkeratin and CCSP (lung broncho-epithelial cells), albumin and alfa-fetoprotein (hepatocytes of liver), Neurophilament-200 (marker of motoneurons) and S-100 (marker of glial cells in brain). Cells positive for human HLA-DR and CD45 were found in spleen. Cells positive for human Y-chromosome were found in almost all organs: their presence in intestine as differentiated intestinal epithelial cells (FIG. 7), in liver as differentiated hepatocytes expressing albumin, and in brain as differentiated neurons and glial cells. Thus, in chimeric mouse transplanted chorionic colony-forming unit cells demonstrated engraftment into all studied organs and differentiation into ectoderm (mononeurons and glial cell in brain), mesoderm (leukocytes in spleen) and endoderm (intestinal epithelial cells and hepatocytes). This example demonstrates that chorionic colony-forming unit cells are capable of induced pluripotency as revealed by their ability to differentiate into lineages of all three germ layers.

Primary Chorionic Colony-Forming Unit Cells

Example 5

Primary Colony-Forming Unit Cells Isolated from Placenta

Figure 8:
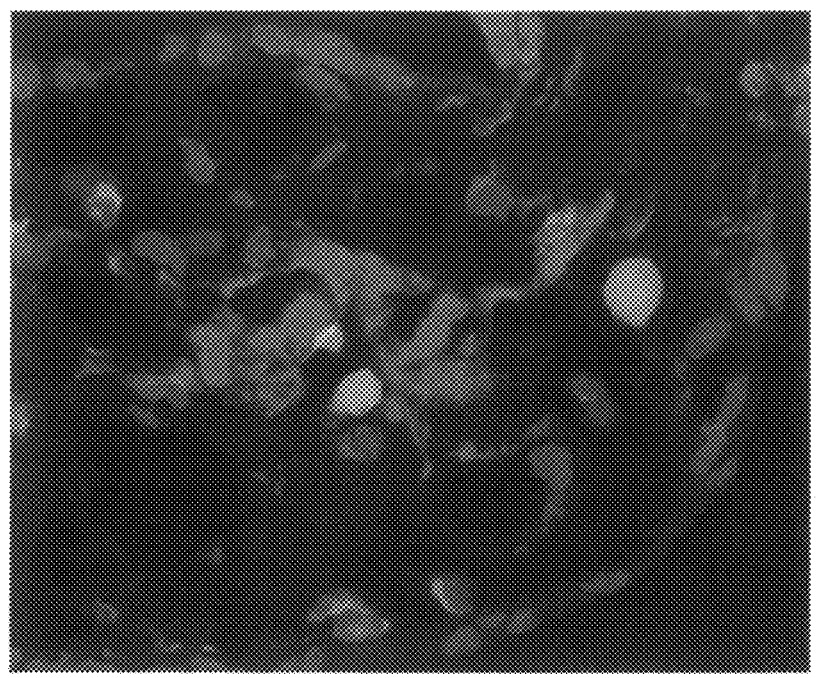
FIG. 8. Clusters of Oct-4—positive sells are present in placental tissue. Paraffin sections human placenta, stained for Oct-4 (Alexa Fluor-red), blue is DAPI staining (nuclei). Oct-4 is highly expressed in nuclei of stromal cells. The size indication bar is 50 μm.

Placental tissues from 15 placentas were immunostained for markers of pluripotent stem cells: Nanog, SSEA-3 and Oct-4. FIG. 8 illustrates clusters of Oct-4-positive cells present in chorionic mesoderm. Cells obtained from digested human placenta as described in Example 1 were further fixed, permeabilized and stained for nuclear and cellular markers of human embryonic stem cells (Nanog, Oct-4) and surface markers—SSEAS-3, SSEA-4, TRA-160.

Cells were isolated from placental digest based upon expression of ACBD6 and further upon expression of surface markers to human pluripotent stem cells: TRA-1-60, SSEA-3. Following FACS sorting, cells were cultured on feeder layers of chorionic plastic-adherent cells. To prepare feeder layers, cells were plated in a 75-cm$^2$ tissue culture flask coated with 0.1% gelatin and media were changed every 2-3 day to eliminate non-adherent cells. After 10-14 days, differentiated cells were digested with 0.25% trypsin/0.5 mM EDTA and split. The medium used for maintaining feeder layers was alpha-DMEM (Gibco BRL) supplemented with 12% fetal bovine serum (FBS) (HyClone), 2 mM L-glutamine. Primary CCFUC expressed a variety of stem cell markers.

Example 6

Therapeutic Use of Undifferentiated Placental Cells for the Treatment of Perfusion Alteration and Myocardial Recovery Following Myocardial Infarction This example is to demonstrate that CCFUC are capable to decrease perfusion abnormalities and development of fibrosis in myocardial infarction following their local instillation into the myocardium. 30 rabbits were used to investigate effect of CCFUC on recovery of myocardium following infarction. To model the myocardial infarction, anesthetized rabbits were intubated, ventilated and thorax was opened in the 4$^{th}$ intercostals space. Pericardium was opened and the front descending branch of left coronary artery was ligated by suture at the distance of 1.0 cm from the heart apex. Following coronary occlusion, 10$^6$ fibroblasts (n=10) or 10$^6$ CCFUC (n=10) were injected into the myocardial tissue distal to the site of occlusion. Ten animals received sham operation. Thorax was closed and animals were allowed to recover for 6 months. Perfusion of myocardium was assessed by injection of $^{131}$I-labeled microspheres. Following injection, animals were euthanized at various times, heart removed and myocardium in the region of infarction as well as control regions was used to determine the activity of microspheres present in tissue. Perfusion was expressed as percentage of specific activity present in myocardium of control group. Myocardium was also used for histological examination of the number of vessels per surface unit area and stained for collagen (Mason TriChrome Stain). The results are shown in Table 5.

Histological examination demonstrated presence of fibrotic changes in the apex of the heart of animals with myocardial infarction, treated by fibroblast injection. Trichrome staining demonstrated large amounts of collagen in these areas. These pathological changes were absent or minimal in animals, injected with CCFUC.

TABLE 5

Human chorionic cells (CCFUC) enhance recovery of perfusion abnormalities and relative capillary density following myocardial infarction. Tissue of left auriculum used as control.

| Group | Control Heart apex | Control Left auriculum | CCFUC heart apex | CCFUC left auriculum | Fibroblasts Heart apex | Fibroblasts left auriculum |
|---|---|---|---|---|---|---|
| Perfusion | 1.01 ± 0.1 | 0.96 ± 0.15 | 0.71 ± 0.09* | 0.89 ± 0.10 | 0.36 ± 0.2 | 0.89 ± 0.1 |
| Relative capillary Density | 1.02 ± 0.08 | 0.978 ± 0.2 | 0.62 ± 0.22 | 0.93 ± 0.2 | 0.44 ± 0.11 | 0.95 ± 0.22 |

Example 6

Therapeutic Use of Undifferentiated Placental Cells for the Treatment of Perfusion Alteration and Myocardial Recovery Following Myocardial Infarction This example is to demonstrate that CCFUC are capable to decrease perfusion abnormalities and development of fibrosis in myocardial infarction following their local instillation into the myocardium. 30 rabbits were used to investigate effect of CCFUC on recovery of myocardium following infarction. To model the myocardial infarction, anesthetized rabbits were intubated, ventilated and thorax was opened in the 4$^{th}$ intercostals space. Pericardium was opened and the front descending branch of left coronary artery was ligated by suture at the distance of 1.0 cm from the heart apex. Following coronary occlusion, 10$^6$ fibroblasts (n=10) or 10$^6$ CCFUC (n=10) were injected into the myocardial tissue distal to the site of occlusion. Ten animals received sham operation. Thorax was closed and animals were allowed to recover for 6 months. Perfusion of myocardium was assessed by injection of $^{131}$I-labeled microspheres. Following injection, animals were euthanized at various times, heart removed and myocardium in the region of infarction as well as control regions was used to determine the activity of microspheres present in tissue. Perfusion was expressed as percentage of specific activity present in myocardium of control group. Myocardium was also used for histological examination of the number of vessels per surface unit area and stained for collagen (Mason TriChrome Stain). The results are shown in Table 5.

Histological examination demonstrated presence of fibrotic changes in the apex of the heart of animals with myocardial infarction, treated by fibroblast injection. Trichrome staining demonstrated large amounts of collagen in these areas. These pathological changes were absent or minimal in animals, injected with CCFUC.

Results are shown in Table 6-7. All animals subjected to spinal cord contusion were affected immediately after injury. Recovery was only partial in the control group, both by neurological score and number of apoptotic cells. In groups which received CCFUC, or neuronally-differentiated placental cells recovery was much faster and complete by day 28, with the highest rate of recovery and lowest rate of apoptotic cells in groups treated with CCFUC or CCFUC which were neuronally-differentiated. In this group histological examina-

TABLE 5

Human chorionic cells (CCFUC) enhance recovery of perfusion abnormalities and relative capillary density following myocardial infarction. Tissue of left auriculum used as control.

| Group | Control Heart apex | Control Left auriculum | CCFUC heart apex | CCFUC left auriculum | Fibroblasts Heart apex | Fibroblasts left auriculum |
|---|---|---|---|---|---|---|
| Perfusion | 1.01 ± 0.1 | 0.96 ± 0.15 | 0.71 ± 0.09* | 0.89 ± 0.10 | 0.36 ± 0.2 | 0.89 ± 0.1 |
| Relative capillary Density | 1.02 ± 0.08 | 0.978 ± 0.2 | 0.62 ± 0.22 | 0.93 ± 0.2 | 0.44 ± 0.11 | 0.95 ± 0.22 |

Example 7

Therapeutic Use of Placental Cells for Enhancement of Recovery of Central and Peripheral Neural System Following Traumatic Injury For differentiation of placental stem cells into neural lineages CCFUC cells were cultured in the presence of NGF/trans-retinoic acid for 7-10 days. Stem cells cultured in the presence of NGF/all-trans-retinoic acid expressed nestin, Neurofilament, GABA receptor, agrin, MUSKinase. Adult Sprague-Dawley rats (females) weighing 240-260 g were used in experiments under general anesthesia. Motor neurological function of the rats was evaluated by using the locomotor rating scale. In this scale, animals are assigned a score ranging from 0 (no observable hindlimb movements) to 21 (normal gait). The rats were tested for functional deficits at 1, 7, 14, 28 days after injury by examiner by blinded technique. Spinal cord contusion model was used to model injury of spinal cord. Metallic rod was placed at the specified height over the spinal cord of anesthetized and immobilized animal. The level of impact was measured by dynamometer. Laminectomy was done at the T9 vertebral level. A rod force of 1 N was applied for 1 s, followed by automatic return. Control group of animal received instillation of $10^6$ fibroblasts at the site of injury, while 3 experimental groups received same number of CCFUC, AMSC, or neuronally-differentiated CCFUC cells. Wound was then closed under aseptic conditions. Neurological function was evaluated 24 h after injury and then twice a week. Some animals in each group were euthanized after 1 week for histological examination. The spinal cord at the injury site was fixed in 4% paraformaldehyde. Apoptosis of oligodendrocytes within the fasciculus cuneatus was determined using the terminal deoxynucleotidyltransferase-mediated dUTP end labeling (TUNEL) method (In Situ Cell Death Detection kit, Roche Diagnostics). Sections obtained from treated and control animals were examined by using light microscopy, and the total number of TUNEL-positive cells was counted.

tion by staining for human Y-chromosome by FISH revealed presence of neuronal-like human cells in spinal cord.

TABLE 6

Human placental cells enhance recovery following spinal cord injury.

| | Neurological score At 2 d | Neurological score At 7 d | Neurological score At 14 d | Neurological score At 28 d |
|---|---|---|---|---|
| Fibroblasts | 1 ± 1 | 4 ± 1 | 6 ± 1 | 7 ± 1 |
| CCFUC | 1 ± 1 | 5 ± 3 | 13 ± 4 | 18 ± 2* |
| AMSC | 1 ± 1 | 3 ± 1 | 11 ± 2 | 10 ± 3 |
| Differentiated Neurons | 1 ± 1 | 6 ± 1 | 16 ± 4 | 20 ± 2* |

*results are statistically significantly different ($P < 0.05$)

TABLE 7

Human placental cells decrease apoptosis of spinal cord cells following spinal cord injury.

| | Apoptotic cells At 10 d |
|---|---|
| Fibroblasts | 15 ± 1 |
| CCFUC | 4 ± 1* |
| AMSC | 8 ± 1* |
| Differentiated Neurons | 2 ± 1* |

Number of apoptotic cells within the fasciculus cumeatus distal to the site of injury by TUNEL method.
(*$P < 0.05$).

Example 8

Therapeutic Use of Placental Cells in Animal Model of Muscle Dystrophy

Studies were done in vivo to show the feasibility of CCFUC transformation into different cells on muscle fibers in mice. Dystrophin is a cytoplasmic protein with domains homologous to spectrin and α-actinin. It is involved in the organization and function of muscle fibers. The absence of dystrophin correlates with morphological and functional abnormalities of striated muscles.

CCFUC were transplanted into sub-lethally or lethally irradiated mice, and engraftment and transformation of CCFUC progeny in muscles was studied. Sub-lethally irradiated C57Bl/6 mice were transfused with $2 \times 10^6$ CCFUC or human fibroblasts. One 1 week to 6 months later, animals from both groups were euthanized and organs were harvested and analyzed for the presence of Y-chromosome-positive cells using confocal microscopy. We found few cells expressing human Y-chromosome ($Y^+$) among myocytes following CCFUC transplantation, but none following fibroblast transplantation. When the animals were subjected to heavy exercise (swimming) $2.5\pm0.5^+$ striated muscle fibers (SMF) were observed per 100 SMF in m. quadriceps femoris 1 week after the exercise, but none in fibroblast group. In transgenic myodystrophy (mdx) mice subjected to similar type of transplantation, similar physical exercise resulted in the appearance of $10\pm3$ $Y^+$ SMF per 100 SMF, but none after fibroblast transplantation.

Transplantation of CCFUC directly into muscle tissues in mdx mice was also done. In non-injured recipients intramuscular transplantation of $10^5$ CCFUC resulted in the appearance of $3.5\pm$ $Y^+$ SMF per 100 SMF. In mdx mice similar injections produced $15.3\pm4.8$ $Y^+$ SMF per 100 SMF after 1 week; but only $2\pm1$ $Y^+$ SMF per 100 SMF after transplantation of fibroblasts. These results demonstrate that in irradiated recipients, transformation/fusion of transplanted CCFUC into myocytes occur following muscle injury and is significantly more pronounced in mice with muscle dystrophy. We further investigated expression of dystrophin in engrafted GFP-positive cells in mdx mice. Transplantation of CCFUC resulted in appearance of dystrophin in SMF, which was related to CCFUC engraftment. Following transplantation of CCFUC from into mdx mice the percent of SMF without central positioning of nuclei (index of differentiation) increased from $9\pm26\%$ in control group to $21\pm3\%$ in experimental group.

The invention claimed is:

1. Isolated colony-forming unit cells derived from the chorion of human term placentas, wherein the isolated colony-forming unit cells are multipotent stem cells characterized by:
   I) expression of protein ACBD6;
   II) low telomerase activity and ability to be propagated over at least 70 doublings in vitro culture without substantial alteration of karyotype;
   III) expression of a combination of at least one of the markers from each of:
   iv) CD-90, SSEA-3, or TRA-1-60;
   v) a Nanog cytosolic polypeptide;
   vi) a neurofilament family cytosolic polypeptide;
   vii) a Nestin cytosolic polypeptide; and
   viii) one or more secreted polypeptides selected from a family of fibroblast growth factors, hepatocyte growth factors, keratinocyte growth factors, and angiopoietins; and
   ix) nuclear peptide Oct-4;
   IV) lack the ability for spontaneous differentiation into lineages of 3 germ layers under standard culture conditions, unless specifically stimulated and lack the ability for formation of teratomas in humans or immuno-compromised animals;
   V) ability to differentiate into lineages of all 3 germ layers when the cells are exposed to lineage-specific differentiation conditions;
   VI) ability to grow without adherence to plastic; and
   VII) inability to form embryoid-like bodies.

2. The isolated colony-forming unit cells of claim 1, wherein the cells are capable of repopulating organs of humans or immunodeficient animals without formation of teratomas.

3. A pharmaceutical composition comprising isolated colony-forming unit cells of claim 1 and a pharmaceutically acceptable carrier.

4. A pharmaceutical composition comprising isolated colony-forming unit cells of claim 1, an effective amount of any other cell population, and a pharmaceutically acceptable carrier.

5. A tissue-engineered construct, comprising isolated colony-forming unit cells of claim 1 and a biocompatible polymer scaffold.

6. A method of enhancing regeneration of diseased tissue of organs, comprising administering to the diseased tissue the cells of claim 1 by local or systemic delivery of said cells.

7. A method of claim 6 where the organ is heart.

8. A method of claim 6 where the organ in spinal cord.

9. A method of claim 6 where the organ is striated muscle.

10. A method of claim 6 where the organ is peripheral nerve.

* * * * *